(12) United States Patent
Arnold et al.

(10) Patent No.: US 9,919,032 B2
(45) Date of Patent: Mar. 20, 2018

(54) METHOD FOR ADMINISTERING A SUSTAINED RELEASE FORMULATION

(71) Applicant: PhaseBio Pharmaceuticals, Inc., Malvern, PA (US)

(72) Inventors: Susan Arnold, Malvern, PA (US); Christopher Prior, Malvern, PA (US); Lynne Georgopoulos, Malvern, PA (US)

(73) Assignee: PHASEBIO PHARMACEUTICALS, INC., Malvern, PA (US)

( * ) Notice: Subject to any disclaimer, the term of this patent is extended or adjusted under 35 U.S.C. 154(b) by 0 days.

(21) Appl. No.: 15/355,386

(22) Filed: Nov. 18, 2016

(65) Prior Publication Data

US 2017/0136092 A1    May 18, 2017

Related U.S. Application Data

(63) Continuation of application No. 14/646,273, filed as application No. PCT/US2013/071038 on Nov. 20, 2013, now abandoned.

(60) Provisional application No. 61/728,318, filed on Nov. 20, 2012.

(51) Int. Cl.
  *A61K 38/22* (2006.01)
  *A61K 38/16* (2006.01)
  *A61K 9/00* (2006.01)

(52) U.S. Cl.
  CPC ........ *A61K 38/2278* (2013.01); *A61K 9/0019* (2013.01); *A61K 38/16* (2013.01)

(58) Field of Classification Search
  CPC ... A61K 38/2278; A61K 36/16; A61K 9/0019
  See application file for complete search history.

(56) References Cited

U.S. PATENT DOCUMENTS

| | | |
|---|---|---|
| 6,328,996 B1 | 12/2001 | Urry |
| 6,355,776 B1 | 3/2002 | Ferrari et al. |
| 2008/0268045 A1 | 10/2008 | Dervieux et al. |
| 2008/0286808 A1 | 11/2008 | Schellenberger et al. |
| 2008/0312157 A1 | 12/2008 | Levy et al. |
| 2009/0004104 A1 | 1/2009 | Chilkoti |
| 2010/0022455 A1 | 1/2010 | Chilkoti |
| 2010/0190701 A1 | 7/2010 | Day et al. |
| 2011/0016602 A1 | 1/2011 | Burns et al. |
| 2011/0123487 A1 | 5/2011 | Chilkoti |
| 2011/0178017 A1 | 7/2011 | Sadeghi et al. |
| 2011/0257092 A1 | 10/2011 | Dimarchi et al. |
| 2013/0090285 A1 | 4/2013 | Georgopoulos et al. |
| 2014/0364362 A1 | 12/2014 | Jowett et al. |
| 2015/0290328 A1 | 10/2015 | Arnold et al. |

FOREIGN PATENT DOCUMENTS

| | | |
|---|---|---|
| WO | WO 1996/032406 A1 | 10/1996 |
| WO | WO 2008/155134 A1 | 12/2008 |
| WO | WO 2012/109624 A2 | 8/2012 |
| WO | WO 2013/003449 A2 | 1/2013 |
| WO | WO 2014/081849 A1 | 5/2014 |

OTHER PUBLICATIONS

Voss et al., BMC Gastroenterology, 2012, 12: 30 (10 pages).*
Domschke et al., "Vasoactive Intestinal Peptide in Man: Pharmacokinetics, Metabolic and Circulatory Effects," Gut, 19: 1049-1053 (1978).
Henning and Sawmiller, "Vasoactive intestinal peptide: cardiovascular effect," Cardiovascular Res., 49: 27-37 (2001).
Murphy and Bloom, "Nonpeptidic glucagon-like peptide 1 receptor agonists: A magic bullet for diabetes?" Proc. Natl. Acad. Sci. USA, 104(3): 689-690 (2007).
Patterson et al., "Functional association of the N-terminal residues with the central region in glucagon-related peptides", Journal of Peptide Science, 17(10): 659-666 (2011).
PCT/US2013/071038, International Search Report and Written Opinion, dated Feb. 10, 2014.
PCT/US2013/071038, International Preliminary Report on Patentability, dated May 26, 2015.

* cited by examiner

*Primary Examiner* — Gyan Chandra
(74) *Attorney, Agent, or Firm* — Cooley LLP

(57) ABSTRACT

The present invention provides pharmaceutical formulations for sustained release when administered at cold temperatures, and methods for delivering a treatment regimen with a combination of sustained release and long half-life formulations. The invention provides improved pharmacokinetics for peptide and small molecule drugs.

20 Claims, 21 Drawing Sheets

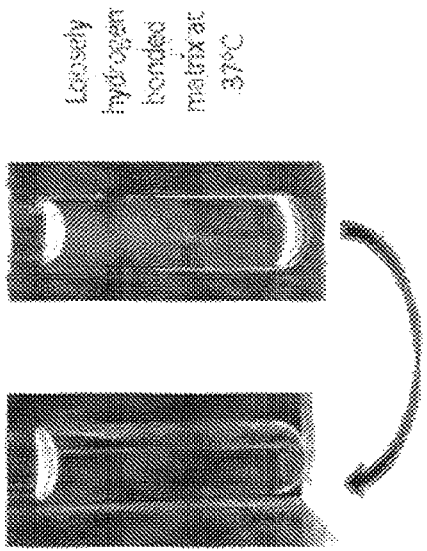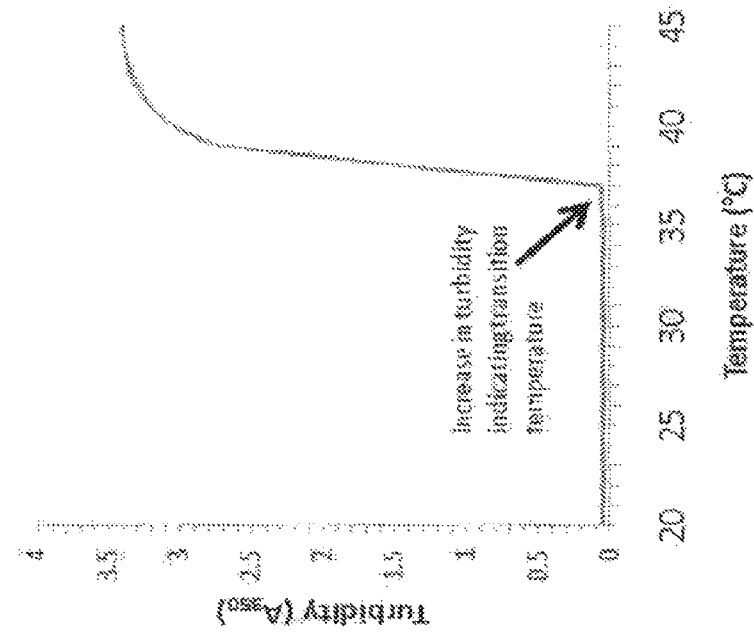
FIG. 1

Transition temperature of ELP1 fusion as a function of protein concentration: mechanism of reversal

FIG. 6

| Study Day | Parameter[a] | Dose | | | |
|---|---|---|---|---|---|
| | | 0.3 mg/kg | 0.6 mg/kg | 0.9 mg/kg | 1.35 mg/kg |
| 0 | Cmax (ng/mL) | 264 ± 69.9 (6) | 360 ± 230 (12) | 291 ± 107 (12) | 960 ± 349 (10) |
| | Tmax (h) | 44.9 (6) | 58.1 (12) | 44.6 (10) | 20.3 (10) |
| | AUC(0-t) (h·ng/mL) | 16,560 ± 4,225 (6) | 31,444 ± 13,963 (12) | 30,235 ± 8,960 (12) | 80,539 ± 31,919 (10) |
| | AUC(inf) (h·ng/mL) | 20,505 ± 1,331 (3) | 29,897 ± 13,573 (10) | 30,235 ± 8,960 (12) | 80,539 ± 31,919 (10) |
| | λz (h⁻¹) | 0.0198 ± 0.0085 (3) | 0.0181 ± 0.0043 (9) | 0.0132 ± 0.0051 (9) | 0.0146 ± 0.0056 (7) |
| | t½ (h) | 41.0 ± 21.5 (3) | 45.3 ± 10.01 (8) | 60.9 ± 24.5 (9) | 54.0 ± 20.8 (7) |
| | CL/F (mL/h/kg) | 14.7 ± 0.96 (3) | 16.6 ± 4.49 (8) | 30.3 ± 10.3 (9) | 14.7 ± 5.48 (7) |
| | Vz/F (L/kg) | 0.87 ± 0.45 (3) | 1.11 ± 0.45 (8) | 2.14 ± 0.78 (9) | 1.19 ± 0.84 (7) |
| 21 | Cmax (ng/mL) | 181 ± 71.9 (6) | 477 ± 245 (11) | 524 ± 380 (11) | 925 ± 415 (9) |
| | Tmax (h) | 35.5 (6) | 23.9 (11) | 24.0 (10) | 47.0 (9) |
| | AUC(168) (h·ng/mL) | 15,849 ± 8,823 (4) | 40,138 ± 17,076 (10) | 44,917 ± 29,119 (11) | 92,816 ± 34,140 (8) |
| | λz (h⁻¹) | 0.0151 ± 0.0023 (9) | 0.0160 ± 0.0046 (8) | 0.0140 ± 0.0038 (9) | 0.0164 ± 0.0039 (2) |
| | t½ (h) | 46.7 ± 8.6 (3) | 46.6 ± 11.7 (8) | 54.1 ± 20.2 (9) | 43.1 ± 7.8 (2) |
| | CL/F (mL/h/kg) | 21.6 ± 8.44 (4) | 17.6 ± 7.64 (10) | 25.2 ± 10.04 (10) | 17.0 ± 8.20 (8) |
| | Vz/F (L/kg) | 1.31 ± 0.69 (3) | 1.20 ± 0.63 (8) | 2.22 ± 1.13 (9) | 0.81 ± 0.25 (2) |

[a] Arithmetic mean ± standard deviation (N) except Tmax for which the median (N) [Range] are reported.
[b] Parameter could not be estimated.

FIG. 9

| Parameter* | 50 mg/mL (Lot No.1-FIN-0896) | 100 mg/mL (Lot No.3-FIN-1309) |
|---|---|---|
| Cmax (ng/mL) | 457 ± 189 (10) | 434 ± 115 (10) |
| Tmax (h) | 49.4 (10) [8.00 – 71.2] | 48.9 (10) [23.9 – 121] |
| AUC(0-t) (h×ng/mL) | 44,175 ± 10,907 (10) | 42,166 ± 7,466 (10) |
| AUC(inf) (h×ng/mL) | 47,136 ± 10,926 (9) | 43,461 ± 8,327 (9) |
| λz (h$^{-1}$) | 0.0188 ± 0.0054 (9) | 0.0230 ± 0.0037 (9) |
| t½ (h) | 40.0 ± 12.7 (9) | 30.8 ± 4.95 (9) |
| CL/F (mL/min) | 33.8 ± 10.2 (9) | 35.7 ± 7.25 (9) |
| Vz/F (L) | 123 ± 80.2 (9) | 95.1 ± 24.1 (9) |

| Parameter* | 50 mg/mL (Lot No. 1-FIN-0806) | 100 mg/mL (Lot No. 3-FIN-1309) | 100 mg/mL - Cold (Lot No. 3-FIN-1309) |
|---|---|---|---|
| Cmax (ng/mL) | 457 ± 189 (10) | 434 ± 115 (10) | 300 ± 102 (8) |
| Tmax (h) | 49.4 (10) [8.00 – 71.2] | 48.9 (10) [23.9 – 121] | 71.1 (8) [48.0 – 119] |
| AUC(0-t) (h×ng/mL) | 44,175 ± 10,907 (10) | 42,166 ± 7,466 (10) | 34,586 ± 12,785 (8) |
| AUC(inf) (h×ng/mL) | 47,136 ± 10,926 (9) | 43,461 ± 8,327 (9) | 35,001 ± 15,224 (5) |
| λz (1/h) | 0.0188 ± 0.0094 (9) | 0.0230 ± 0.0047 (9) | 0.0202 ± 0.0080 (5) |
| t½ (h) | 40.0 ± 12.7 (9) | 30.8 ± 4.95 (9) | 40.2 ± 20.1 (5) |
| CL/F (mL/min) | 33.8 ± 10.2 (9) | 35.7 ± 7.26 (9) | 51.2 ± 25.8 (5) |
| Vz/F (L) | 123 ± 80.2 (9) | 95.1 ± 24.1 (9) | 209 ± 222 (5) |

*Arithmetic mean ± standard deviation (N) except for Tmax for which the median (N) [Range] is reported.

FIG. 10

| Parameter | Geometric Mean Ratio (%)* | | | Within Subject CV(%) |
|---|---|---|---|---|
| | Estimate | 90% Confidence Interval | | |
| 100 mg/mL-to-30 mg/mL | | | | |
| Cmax | 99.97 | 80.14 → | 124.69 | 27.05 |
| AUC(0-t) | 97.02 | 86.75 → | 108.52 | 13.52 |
| AUC(inf) | 94.79 | 82.84 → | 108.46 | 13.94 |
| 100 mg/mL Cold-to-Room Temperature | | | | |
| Cmax | 68.66 | 48.29 → | 97.61 | 38.47 |
| AUC(0-t) | 79.90 | 58.05 → | 109.96 | 34.70 |
| AUC(inf) | 73.30 | 42.89 → | 126.42 | 42.13 |

*Based on analysis of natural log-transformed data. Lower confidence limits <83.00% and upper confidence limits >125.00% are shown in red.

| Parameter* | 50 mg/mL (Lot No. 1-FTN-0896) | 100 mg/mL (Lot No. 3-FTN-1309) |
|---|---|---|
| Cmax (ng/mL) | 457 ± 189 (10) | 434 ± 115 (10) |
| Tmax (h) | 49.4 (10) [8.00 – 71.2] | 48.9 (10) [23.9 – 121] |
| AUC(0-t) (h×ng/mL) | 44,175 ± 10,907 (10) | 42,166 ± 7,466 (10) |
| AUC(inf) (h×ng/mL) | 47,136 ± 10,926 (9) | 43,461 ± 8,327 (9) |
| λz (1/h) | 0.0188 ± 0.0054 (9) | 0.0230 ± 0.0037 (9) |
| t½ (h) | 40.0 ± 12.7 (9) | 30.8 ± 4.95 (9) |
| CL/F (mL/min) | 33.8 ± 10.2 (9) | 35.7 ± 7.25 (9) |
| Vz/F (L) | 123 ± 80.2 (9) | 95.1 ± 24.1 (9) |

*Arithmetic mean ± standard deviation (N) except for Tmax for which the median (N) [range] is reported

FIG. 15

| Parameter | Geometric Mean Ratio (%)* | | Within Subject CV(%) |
|---|---|---|---|
| | Estimate | 90% Confidence Interval | |
| 100 mg/mL-to-50 mg/mL | | | |
| Cmax | 99.97 | 80.14 → 124.69 | 27.05 |
| AUC(0-t) | 97.02 | 86.75 → 108.52 | 13.52 |
| AUC(inf) | 94.79 | 82.84 → 108.46 | 13.94 |

*Based on analysis of natural log-transformed data. Lower confidence limits < 85.00% and upper confidence limits > 125.00% are shown in red

| Parameter[a] | 100 ng/mL (Lot No. 3-FIN-1309) | 100 ng/mL – Cold (Lot No. 3-FIN-1309) |
|---|---|---|
| Cmax (ng/mL) | 434 ± 115 (10) | 390 ± 102 (8) |
| Tmax (h) | 48.9 (10) [23.0 – 121] | 71.1 (8) [48.0 – 119] |
| AUC(0-t) (h×ng/mL) | 42,166 ± 7,466 (10) | 34,586 ± 12,785 (8) |
| AUC(inf) (h×ng/mL) | 43,461 ± 8,327 (9) | 35,001 ± 15,224 (5) |
| λz (1/h) | 0.0230 ± 0.0037 (9) | 0.0202 ± 0.0080 (5) |
| t½ (h) | 30.8 ± 4.95 (9) | 40.2 ± 20.1 (5) |
| CL/F (mL/min) | 35.7 ± 7.25 (9) | 51.2 ± 25.8 (5) |
| Vz/F (L) | 93.1 ± 24.1 (9) | 209 ± 222 (5) |

[a] Arithmetic mean ± standard deviation (N) except for Tmax for which the median (N) [Range] is reported.

| Parameter | Geometric Mean Ratio (%)* | | | Within Subject CV (%) |
|---|---|---|---|---|
| | Estimate | 90% Confidence Interval | | |
| 100 mg/mL Cold-to-Room Temperature | | | | |
| Cmax | 68.66 | 48.29 → | 97.61 | 38.47 |
| AUC(0-t) | 79.90 | 58.05 → | 109.96 | 34.70 |
| AUC(inf) | 73.30 | 42.80 → | 126.42 | 42.13 |

*Based on analysis of natural log-transformed data. Lower confidence limits < 85.19% and upper confidence limits > 125.16% are shown in red.

FIG. 20A

FVNQHLCGSHLVEALYLVCGERGFFYTPKT R/REAEDLQVGQVELGGGPGAGSLQPLALEGSLQKR GIVEQCCTSICSLYQLENYCN

B chain | C peptide | A chain

FIG. 20B

FVNQHLCGSHLVEALYLVCGERGFFYTPKTRREAEDLQVGQVELGGGPGAGSLQPLALEGSLQKR
GIVEQCCTSICSLYQLENYCNVPGVGVPGVGVPGVGVPGAGVPGGVPGGVPGGVPGGVPGGVPGG
VPGAGVPGGVPGVGVPGVGVPGVGVPGVGVPGVGVPGGVPGGVPGGVPGVGVPGVGVPGVGVPGG
GVPGAGVPGGVPGVGVPGVGVPGVGVPGVGVPGVGVPGGVPGGVPGGVPGVGVPGVGVPGVGVPG
GGVPGAGVPGGVPGVGVPGVGVPGVGVPGVGVPGVGVPGGVPGGVPGGVPGVGVPGVGVPGVGVP
GGGVPGAGVPGGVPGVGVPGVGVPGVGVPGVGVPGVGVPGGVPGGVPGGVPGVGVPGVGVPGVGV
PGGGVPGAGVPGGVPGVGVPGVGVPGVGVPGVGVPGVGVPGGVPGGVPGGVPGVGVPGVGVPGVG
VPGGGVPGAGVPGGVPGVGVPGVGVPGVGVPGVGVPGVGVPGGVPGGVPGGVPGVGVPGVGVPGV
GVPGGGVPGAGVPGGVPGVGVPGVGVPGVGVPGVGVPGVGVPGGVPGGVPGGVPGVGVPGVGVPG
VGVPGGGVPGAGVPGGVPGVGVPGVGVPGVGVPGVGVPGVGVPGGVPGGVPGGVPGVGVPGVGVP
GVGVPGGGVPGAGVPGGVPGWP

FIG. 21

```
  1  MGRLLTSTLV SSYLECLLAK EFIAMLVKGK GVPGCGVPGV GVPGGVPGAG VPGGVPGAGV PGGVPGA
 51  GVPGCGVPGV GVPGAGVPGG VPGAGVPGGV PGAGVPGGVP GAGVPGGVPG AGVPGGVPGA
101  GVPGVGVPGG VPGVGVPGGV PGVGVPGGVP GVGVPGGVPG VGVPGGVPGA GVPGGVPGA
151  GVPGVGVPGV GVPGAGVPGG VPGAGVPGGV PGAGVPGGVP GAGVPGGVPG AGVPGGVPGA
201  GVPGCGVPGG VPGVGVPGGV PGAGVPGGVP GAGVPGGVPG AGVPGGVPGC GVPGGVPGA
251  GVPGVGVPGV GVPGVGVPGG VPGVGVPGGV PGAGVPGGVP GAGVPGGVPG AGVPGGVPGA
301  GVPGVGVPGA GVPGAGVPGG VPGAGVPGGV PGAGVPGGVP GAGVPGGVPG AGVPGGVPGA
351  GVPGAGVPGA GVPGAGVPGG VPGAGVPGGV PGAGVPGGVP GAGVPGGVPG AGVPGGVPGA
401  GVPGVGVPGV GVPGVGVPGG VPGVGVPGGV PGVGVPGGVP GVGVPGGVPG VGVPGGVPGA
451  GVPGVGVPGV GVPGAGVPGG VPGAGVPGGV PGAGVPGGVP GAGVPGGVPG AGVPGGVPGA
501  GVPGVGVPGV GVPGAGVPGG VPGAGVPGGV PGAGVPGGVP GAGVPGGVPG AGVPGGVPGA
551  GVPGVGVPGV GVPGVGVPGG VPGVGVPGGV PGAGVPGGVP GAGVPGGVPG AGVPGGVPGA
601  GVPGVGVPGV GVPGVGVPGG VPGAGVPGG GVPGWP
```

US 9,919,032 B2

SEQUENCE LISTING

```
<160> NUMBER OF SEQ ID NOS: 25

<210> SEQ ID NO 1
<211> LENGTH: 4
<212> TYPE: PRT
<213> ORGANISM: Artificial Sequence
<220> FEATURE:
<223> OTHER INFORMATION: ELP component sequence

<400> SEQUENCE: 1

Val Pro Gly Gly
1

<210> SEQ ID NO 2
<211> LENGTH: 4
<212> TYPE: PRT
<213> ORGANISM: Artificial Sequence
<220> FEATURE:
<223> OTHER INFORMATION: ELP component sequence

<400> SEQUENCE: 2

Ile Pro Gly Gly
1
```

```
<210> SEQ ID NO 3
<211> LENGTH: 5
<212> TYPE: PRT
<213> ORGANISM: Artificial Sequence
<220> FEATURE:
<223> OTHER INFORMATION: ELP component sequence
<220> FEATURE:
<221> NAME/KEY: misc_feature
<222> LOCATION: (4)..(4)
<223> OTHER INFORMATION: Xaa can be any naturally occurring or non-
      natural amino acid

<400> SEQUENCE: 3

Val Pro Gly Xaa Gly
1               5

<210> SEQ ID NO 4
<211> LENGTH: 5
<212> TYPE: PRT
<213> ORGANISM: Artificial Sequence
<220> FEATURE:
<223> OTHER INFORMATION: ELP component sequence

<400> SEQUENCE: 4

Ala Val Gly Val Pro
1               5

<210> SEQ ID NO 5
<211> LENGTH: 5
<212> TYPE: PRT
<213> ORGANISM: Artificial Sequence
<220> FEATURE:
<223> OTHER INFORMATION: ELP component sequence
<220> FEATURE:
<221> NAME/KEY: misc_feature
<222> LOCATION: (4)..(4)
<223> OTHER INFORMATION: Xaa can be any naturally occurring or non-
      natural amino acid

<400> SEQUENCE: 5

Ile Pro Gly Xaa Gly
1               5

<210> SEQ ID NO 6
<211> LENGTH: 5
<212> TYPE: PRT
<213> ORGANISM: Artificial Sequence
<220> FEATURE:
<223> OTHER INFORMATION: ELP component sequence

<400> SEQUENCE: 6

Ile Pro Gly Val Gly
1               5

<210> SEQ ID NO 7
<211> LENGTH: 5
<212> TYPE: PRT
<213> ORGANISM: Artificial Sequence
<220> FEATURE:
<223> OTHER INFORMATION: ELP component sequence
<220> FEATURE:
<221> NAME/KEY: misc_feature
<222> LOCATION: (4)..(4)
<223> OTHER INFORMATION: Xaa can be any naturally occurring or non-
      natural amino acid

<400> SEQUENCE: 7

Leu Pro Gly Xaa Gly
```

```
1               5

<210> SEQ ID NO 8
<211> LENGTH: 5
<212> TYPE: PRT
<213> ORGANISM: Artificial Sequence
<220> FEATURE:
<223> OTHER INFORMATION: ELP component sequence

<400> SEQUENCE: 8

Leu Pro Gly Val Gly
1               5

<210> SEQ ID NO 9
<211> LENGTH: 6
<212> TYPE: PRT
<213> ORGANISM: Artificial Sequence
<220> FEATURE:
<223> OTHER INFORMATION: ELP component sequence

<400> SEQUENCE: 9

Val Ala Pro Gly Val Gly
1               5

<210> SEQ ID NO 10
<211> LENGTH: 8
<212> TYPE: PRT
<213> ORGANISM: Artificial Sequence
<220> FEATURE:
<223> OTHER INFORMATION: ELP component sequence

<400> SEQUENCE: 10

Gly Val Gly Val Pro Gly Val Gly
1               5

<210> SEQ ID NO 11
<211> LENGTH: 9
<212> TYPE: PRT
<213> ORGANISM: Artificial Sequence
<220> FEATURE:
<223> OTHER INFORMATION: ELP component sequence

<400> SEQUENCE: 11

Val Pro Gly Phe Gly Val Gly Ala Gly
1               5

<210> SEQ ID NO 12
<211> LENGTH: 9
<212> TYPE: PRT
<213> ORGANISM: Artificial Sequence
<220> FEATURE:
<223> OTHER INFORMATION: ELP component sequence

<400> SEQUENCE: 12

Val Pro Gly Val Gly Val Pro Gly Gly
1               5

<210> SEQ ID NO 13
<211> LENGTH: 450
<212> TYPE: PRT
<213> ORGANISM: Artificial Sequence
<220> FEATURE:
<223> OTHER INFORMATION: ELP biopolymer sequence
<220> FEATURE:
<221> NAME/KEY: misc_feature
<222> LOCATION: (4)..(4)
<223> OTHER INFORMATION: Xaa can be any naturally occurring or non-
      natural amino acid
```

```
<220> FEATURE:
<221> NAME/KEY: misc_feature
<222> LOCATION: (9)..(9)
<223> OTHER INFORMATION: Xaa can be any naturally occurring or non-
      natural amino acid
<220> FEATURE:
<221> NAME/KEY: misc_feature
<222> LOCATION: (14)..(14)
<223> OTHER INFORMATION: Xaa can be any naturally occurring or non-
      natural amino acid
<220> FEATURE:
<221> NAME/KEY: misc_feature
<222> LOCATION: (19)..(19)
<223> OTHER INFORMATION: Xaa can be any naturally occurring or non-
      natural amino acid
<220> FEATURE:
<221> NAME/KEY: misc_feature
<222> LOCATION: (24)..(24)
<223> OTHER INFORMATION: Xaa can be any naturally occurring or non-
      natural amino acid
<220> FEATURE:
<221> NAME/KEY: misc_feature
<222> LOCATION: (29)..(29)
<223> OTHER INFORMATION: Xaa can be any naturally occurring or non-
      natural amino acid
<220> FEATURE:
<221> NAME/KEY: misc_feature
<222> LOCATION: (34)..(34)
<223> OTHER INFORMATION: Xaa can be any naturally occurring or non-
      natural amino acid
<220> FEATURE:
<221> NAME/KEY: misc_feature
<222> LOCATION: (39)..(39)
<223> OTHER INFORMATION: Xaa can be any naturally occurring or non-
      natural amino acid
<220> FEATURE:
<221> NAME/KEY: misc_feature
<222> LOCATION: (44)..(44)
<223> OTHER INFORMATION: Xaa can be any naturally occurring or non-
      natural amino acid
<220> FEATURE:
<221> NAME/KEY: misc_feature
<222> LOCATION: (49)..(49)
<223> OTHER INFORMATION: Xaa can be any naturally occurring or non-
      natural amino acid
<220> FEATURE:
<221> NAME/KEY: misc_feature
<222> LOCATION: (54)..(54)
<223> OTHER INFORMATION: Xaa can be any naturally occurring or non-
      natural amino acid
<220> FEATURE:
<221> NAME/KEY: misc_feature
<222> LOCATION: (59)..(59)
<223> OTHER INFORMATION: Xaa can be any naturally occurring or non-
      natural amino acid
<220> FEATURE:
<221> NAME/KEY: misc_feature
<222> LOCATION: (64)..(64)
<223> OTHER INFORMATION: Xaa can be any naturally occurring or non-
      natural amino acid
<220> FEATURE:
<221> NAME/KEY: misc_feature
<222> LOCATION: (69)..(69)
<223> OTHER INFORMATION: Xaa can be any naturally occurring or non-
      natural amino acid
<220> FEATURE:
<221> NAME/KEY: misc_feature
<222> LOCATION: (74)..(74)
<223> OTHER INFORMATION: Xaa can be any naturally occurring or non-
      natural amino acid
<220> FEATURE:
<221> NAME/KEY: misc_feature
<222> LOCATION: (79)..(79)
<223> OTHER INFORMATION: Xaa can be any naturally occurring or non-
      natural amino acid
<220> FEATURE:
<221> NAME/KEY: misc_feature
<222> LOCATION: (84)..(84)
<223> OTHER INFORMATION: Xaa can be any naturally occurring or non-
```

```
       natural amino acid
<220> FEATURE:
<221> NAME/KEY: misc_feature
<222> LOCATION: (89)..(89)
<223> OTHER INFORMATION: Xaa can be any naturally occurring or non-
      natural amino acid
<220> FEATURE:
<221> NAME/KEY: misc_feature
<222> LOCATION: (94)..(94)
<223> OTHER INFORMATION: Xaa can be any naturally occurring or non-
      natural amino acid
<220> FEATURE:
<221> NAME/KEY: misc_feature
<222> LOCATION: (99)..(99)
<223> OTHER INFORMATION: Xaa can be any naturally occurring or non-
      natural amino acid
<220> FEATURE:
<221> NAME/KEY: misc_feature
<222> LOCATION: (104)..(104)
<223> OTHER INFORMATION: Xaa can be any naturally occurring or non-
      natural amino acid
<220> FEATURE:
<221> NAME/KEY: misc_feature
<222> LOCATION: (109)..(109)
<223> OTHER INFORMATION: Xaa can be any naturally occurring or non-
      natural amino acid
<220> FEATURE:
<221> NAME/KEY: misc_feature
<222> LOCATION: (114)..(114)
<223> OTHER INFORMATION: Xaa can be any naturally occurring or non-
      natural amino acid
<220> FEATURE:
<221> NAME/KEY: misc_feature
<222> LOCATION: (119)..(119)
<223> OTHER INFORMATION: Xaa can be any naturally occurring or non-
      natural amino acid
<220> FEATURE:
<221> NAME/KEY: misc_feature
<222> LOCATION: (124)..(124)
<223> OTHER INFORMATION: Xaa can be any naturally occurring or non-
      natural amino acid
<220> FEATURE:
<221> NAME/KEY: misc_feature
<222> LOCATION: (129)..(129)
<223> OTHER INFORMATION: Xaa can be any naturally occurring or non-
      natural amino acid
<220> FEATURE:
<221> NAME/KEY: misc_feature
<222> LOCATION: (134)..(134)
<223> OTHER INFORMATION: Xaa can be any naturally occurring or non-
      natural amino acid
<220> FEATURE:
<221> NAME/KEY: misc_feature
<222> LOCATION: (139)..(139)
<223> OTHER INFORMATION: Xaa can be any naturally occurring or non-
      natural amino acid
<220> FEATURE:
<221> NAME/KEY: misc_feature
<222> LOCATION: (144)..(144)
<223> OTHER INFORMATION: Xaa can be any naturally occurring or non-
      natural amino acid
<220> FEATURE:
<221> NAME/KEY: misc_feature
<222> LOCATION: (149)..(149)
<223> OTHER INFORMATION: Xaa can be any naturally occurring or non-
      natural amino acid
<220> FEATURE:
<221> NAME/KEY: misc_feature
<222> LOCATION: (154)..(154)
<223> OTHER INFORMATION: Xaa can be any naturally occurring or non-
      natural amino acid
<220> FEATURE:
<221> NAME/KEY: misc_feature
<222> LOCATION: (159)..(159)
<223> OTHER INFORMATION: Xaa can be any naturally occurring or non-
      natural amino acid
<220> FEATURE:
<221> NAME/KEY: misc_feature
<222> LOCATION: (164)..(164)
```

```
<223> OTHER INFORMATION: Xaa can be any naturally occurring or non-
      natural amino acid
<220> FEATURE:
<221> NAME/KEY: misc_feature
<222> LOCATION: (169)..(169)
<223> OTHER INFORMATION: Xaa can be any naturally occurring or non-
      natural amino acid
<220> FEATURE:
<221> NAME/KEY: misc_feature
<222> LOCATION: (174)..(174)
<223> OTHER INFORMATION: Xaa can be any naturally occurring or non-
      natural amino acid
<220> FEATURE:
<221> NAME/KEY: misc_feature
<222> LOCATION: (179)..(179)
<223> OTHER INFORMATION: Xaa can be any naturally occurring or non-
      natural amino acid
<220> FEATURE:
<221> NAME/KEY: misc_feature
<222> LOCATION: (184)..(184)
<223> OTHER INFORMATION: Xaa can be any naturally occurring or non-
      natural amino acid
<220> FEATURE:
<221> NAME/KEY: misc_feature
<222> LOCATION: (189)..(189)
<223> OTHER INFORMATION: Xaa can be any naturally occurring or non-
      natural amino acid
<220> FEATURE:
<221> NAME/KEY: misc_feature
<222> LOCATION: (194)..(194)
<223> OTHER INFORMATION: Xaa can be any naturally occurring or non-
      natural amino acid
<220> FEATURE:
<221> NAME/KEY: misc_feature
<222> LOCATION: (199)..(199)
<223> OTHER INFORMATION: Xaa can be any naturally occurring or non-
      natural amino acid
<220> FEATURE:
<221> NAME/KEY: misc_feature
<222> LOCATION: (204)..(204)
<223> OTHER INFORMATION: Xaa can be any naturally occurring or non-
      natural amino acid
<220> FEATURE:
<221> NAME/KEY: misc_feature
<222> LOCATION: (209)..(209)
<223> OTHER INFORMATION: Xaa can be any naturally occurring or non-
      natural amino acid
<220> FEATURE:
<221> NAME/KEY: misc_feature
<222> LOCATION: (214)..(214)
<223> OTHER INFORMATION: Xaa can be any naturally occurring or non-
      natural amino acid
<220> FEATURE:
<221> NAME/KEY: misc_feature
<222> LOCATION: (219)..(219)
<223> OTHER INFORMATION: Xaa can be any naturally occurring or non-
      natural amino acid
<220> FEATURE:
<221> NAME/KEY: misc_feature
<222> LOCATION: (224)..(224)
<223> OTHER INFORMATION: Xaa can be any naturally occurring or non-
      natural amino acid
<220> FEATURE:
<221> NAME/KEY: misc_feature
<222> LOCATION: (229)..(229)
<223> OTHER INFORMATION: Xaa can be any naturally occurring or non-
      natural amino acid
<220> FEATURE:
<221> NAME/KEY: misc_feature
<222> LOCATION: (234)..(234)
<223> OTHER INFORMATION: Xaa can be any naturally occurring or non-
      natural amino acid
<220> FEATURE:
<221> NAME/KEY: misc_feature
<222> LOCATION: (239)..(239)
<223> OTHER INFORMATION: Xaa can be any naturally occurring or non-
      natural amino acid
<220> FEATURE:
<221> NAME/KEY: misc_feature
```

```
<222> LOCATION: (244)..(244)
<223> OTHER INFORMATION: Xaa can be any naturally occurring or non-
      natural amino acid
<220> FEATURE:
<221> NAME/KEY: misc_feature
<222> LOCATION: (249)..(249)
<223> OTHER INFORMATION: Xaa can be any naturally occurring or non-
      natural amino acid
<220> FEATURE:
<221> NAME/KEY: misc_feature
<222> LOCATION: (254)..(254)
<223> OTHER INFORMATION: Xaa can be any naturally occurring or non-
      natural amino acid
<220> FEATURE:
<221> NAME/KEY: misc_feature
<222> LOCATION: (259)..(259)
<223> OTHER INFORMATION: Xaa can be any naturally occurring or non-
      natural amino acid
<220> FEATURE:
<221> NAME/KEY: misc_feature
<222> LOCATION: (264)..(264)
<223> OTHER INFORMATION: Xaa can be any naturally occurring or non-
      natural amino acid
<220> FEATURE:
<221> NAME/KEY: misc_feature
<222> LOCATION: (269)..(269)
<223> OTHER INFORMATION: Xaa can be any naturally occurring or non-
      natural amino acid
<220> FEATURE:
<221> NAME/KEY: misc_feature
<222> LOCATION: (274)..(274)
<223> OTHER INFORMATION: Xaa can be any naturally occurring or non-
      natural amino acid
<220> FEATURE:
<221> NAME/KEY: misc_feature
<222> LOCATION: (279)..(279)
<223> OTHER INFORMATION: Xaa can be any naturally occurring or non-
      natural amino acid
<220> FEATURE:
<221> NAME/KEY: misc_feature
<222> LOCATION: (284)..(284)
<223> OTHER INFORMATION: Xaa can be any naturally occurring or non-
      natural amino acid
<220> FEATURE:
<221> NAME/KEY: misc_feature
<222> LOCATION: (289)..(289)
<223> OTHER INFORMATION: Xaa can be any naturally occurring or non-
      natural amino acid
<220> FEATURE:
<221> NAME/KEY: misc_feature
<222> LOCATION: (294)..(294)
<223> OTHER INFORMATION: Xaa can be any naturally occurring or non-
      natural amino acid
<220> FEATURE:
<221> NAME/KEY: misc_feature
<222> LOCATION: (299)..(299)
<223> OTHER INFORMATION: Xaa can be any naturally occurring or non-
      natural amino acid
<220> FEATURE:
<221> NAME/KEY: misc_feature
<222> LOCATION: (304)..(304)
<223> OTHER INFORMATION: Xaa can be any naturally occurring or non-
      natural amino acid
<220> FEATURE:
<221> NAME/KEY: misc_feature
<222> LOCATION: (309)..(309)
<223> OTHER INFORMATION: Xaa can be any naturally occurring or non-
      natural amino acid
<220> FEATURE:
<221> NAME/KEY: misc_feature
<222> LOCATION: (314)..(314)
<223> OTHER INFORMATION: Xaa can be any naturally occurring or non-
      natural amino acid
<220> FEATURE:
<221> NAME/KEY: misc_feature
<222> LOCATION: (319)..(319)
<223> OTHER INFORMATION: Xaa can be any naturally occurring or non-
      natural amino acid
<220> FEATURE:
```

```
<221> NAME/KEY: misc_feature
<222> LOCATION: (324)..(324)
<223> OTHER INFORMATION: Xaa can be any naturally occurring or non-
      natural amino acid
<220> FEATURE:
<221> NAME/KEY: misc_feature
<222> LOCATION: (329)..(329)
<223> OTHER INFORMATION: Xaa can be any naturally occurring or non-
      natural amino acid
<220> FEATURE:
<221> NAME/KEY: misc_feature
<222> LOCATION: (334)..(334)
<223> OTHER INFORMATION: Xaa can be any naturally occurring or non-
      natural amino acid
<220> FEATURE:
<221> NAME/KEY: misc_feature
<222> LOCATION: (339)..(339)
<223> OTHER INFORMATION: Xaa can be any naturally occurring or non-
      natural amino acid
<220> FEATURE:
<221> NAME/KEY: misc_feature
<222> LOCATION: (344)..(344)
<223> OTHER INFORMATION: Xaa can be any naturally occurring or non-
      natural amino acid
<220> FEATURE:
<221> NAME/KEY: misc_feature
<222> LOCATION: (349)..(349)
<223> OTHER INFORMATION: Xaa can be any naturally occurring or non-
      natural amino acid
<220> FEATURE:
<221> NAME/KEY: misc_feature
<222> LOCATION: (354)..(354)
<223> OTHER INFORMATION: Xaa can be any naturally occurring or non-
      natural amino acid
<220> FEATURE:
<221> NAME/KEY: misc_feature
<222> LOCATION: (359)..(359)
<223> OTHER INFORMATION: Xaa can be any naturally occurring or non-
      natural amino acid
<220> FEATURE:
<221> NAME/KEY: misc_feature
<222> LOCATION: (364)..(364)
<223> OTHER INFORMATION: Xaa can be any naturally occurring or non-
      natural amino acid
<220> FEATURE:
<221> NAME/KEY: misc_feature
<222> LOCATION: (369)..(369)
<223> OTHER INFORMATION: Xaa can be any naturally occurring or non-
      natural amino acid
<220> FEATURE:
<221> NAME/KEY: misc_feature
<222> LOCATION: (374)..(374)
<223> OTHER INFORMATION: Xaa can be any naturally occurring or non-
      natural amino acid
<220> FEATURE:
<221> NAME/KEY: misc_feature
<222> LOCATION: (379)..(379)
<223> OTHER INFORMATION: Xaa can be any naturally occurring or non-
      natural amino acid
<220> FEATURE:
<221> NAME/KEY: misc_feature
<222> LOCATION: (384)..(384)
<223> OTHER INFORMATION: Xaa can be any naturally occurring or non-
      natural amino acid
<220> FEATURE:
<221> NAME/KEY: misc_feature
<222> LOCATION: (389)..(389)
<223> OTHER INFORMATION: Xaa can be any naturally occurring or non-
      natural amino acid
<220> FEATURE:
<221> NAME/KEY: misc_feature
<222> LOCATION: (394)..(394)
<223> OTHER INFORMATION: Xaa can be any naturally occurring or non-
      natural amino acid
<220> FEATURE:
<221> NAME/KEY: misc_feature
<222> LOCATION: (399)..(399)
<223> OTHER INFORMATION: Xaa can be any naturally occurring or non-
      natural amino acid
```

```
<220> FEATURE:
<221> NAME/KEY: misc_feature
<222> LOCATION: (404)..(404)
<223> OTHER INFORMATION: Xaa can be any naturally occurring or non-
      natural amino acid
<220> FEATURE:
<221> NAME/KEY: misc_feature
<222> LOCATION: (409)..(409)
<223> OTHER INFORMATION: Xaa can be any naturally occurring or non-
      natural amino acid
<220> FEATURE:
<221> NAME/KEY: misc_feature
<222> LOCATION: (414)..(414)
<223> OTHER INFORMATION: Xaa can be any naturally occurring or non-
      natural amino acid
<220> FEATURE:
<221> NAME/KEY: misc_feature
<222> LOCATION: (419)..(419)
<223> OTHER INFORMATION: Xaa can be any naturally occurring or non-
      natural amino acid
<220> FEATURE:
<221> NAME/KEY: misc_feature
<222> LOCATION: (424)..(424)
<223> OTHER INFORMATION: Xaa can be any naturally occurring or non-
      natural amino acid
<220> FEATURE:
<221> NAME/KEY: misc_feature
<222> LOCATION: (429)..(429)
<223> OTHER INFORMATION: Xaa can be any naturally occurring or non-
      natural amino acid
<220> FEATURE:
<221> NAME/KEY: misc_feature
<222> LOCATION: (434)..(434)
<223> OTHER INFORMATION: Xaa can be any naturally occurring or non-
      natural amino acid
<220> FEATURE:
<221> NAME/KEY: misc_feature
<222> LOCATION: (439)..(439)
<223> OTHER INFORMATION: Xaa can be any naturally occurring or non-
      natural amino acid
<220> FEATURE:
<221> NAME/KEY: misc_feature
<222> LOCATION: (444)..(444)
<223> OTHER INFORMATION: Xaa can be any naturally occurring or non-
      natural amino acid
<220> FEATURE:
<221> NAME/KEY: misc_feature
<222> LOCATION: (449)..(449)
<223> OTHER INFORMATION: Xaa can be any naturally occurring or non-
      natural amino acid

<400> SEQUENCE: 13

Val Pro Gly Xaa Gly Val Pro Gly Xaa Gly Val Pro Gly Xaa Gly Val
1               5                   10                  15

Pro Gly Xaa Gly Val Pro Gly Xaa Gly Val Pro Gly Xaa Gly Val Pro
            20                  25                  30

Gly Xaa Gly Val Pro Gly Xaa Gly Val Pro Gly Xaa Gly Val Pro Gly
        35                  40                  45

Xaa Gly Val Pro Gly Xaa Gly Val Pro Gly Xaa Gly Val Pro Gly Xaa
    50                  55                  60

Gly Val Pro Gly Xaa Gly Val Pro Gly Xaa Gly Val Pro Gly Xaa Gly
65                  70                  75                  80

Val Pro Gly Xaa Gly Val Pro Gly Xaa Gly Val Pro Gly Xaa Gly Val
                85                  90                  95

Pro Gly Xaa Gly Val Pro Gly Xaa Gly Val Pro Gly Xaa Gly Val Pro
            100                 105                 110

Gly Xaa Gly Val Pro Gly Xaa Gly Val Pro Gly Xaa Gly Val Pro Gly
        115                 120                 125

Xaa Gly Val Pro Gly Xaa Gly Val Pro Gly Xaa Gly Val Pro Gly Xaa
```

```
                130                 135                 140

Gly Val Pro Gly Xaa Gly Val Pro Gly Xaa Gly Val Pro Gly Xaa Gly
145                 150                 155                 160

Val Pro Gly Xaa Gly Val Pro Gly Xaa Gly Val Pro Gly Xaa Gly Val
                165                 170                 175

Pro Gly Xaa Gly Val Pro Gly Xaa Gly Val Pro Gly Xaa Gly Val Pro
            180                 185                 190

Gly Xaa Gly Val Pro Gly Xaa Gly Val Pro Gly Xaa Gly Val Pro Gly
        195                 200                 205

Xaa Gly Val Pro Gly Xaa Gly Val Pro Gly Xaa Gly Val Pro Gly Xaa
    210                 215                 220

Gly Val Pro Gly Xaa Gly Val Pro Gly Xaa Gly Val Pro Gly Xaa Gly
225                 230                 235                 240

Val Pro Gly Xaa Gly Val Pro Gly Xaa Gly Val Pro Gly Xaa Gly Val
                245                 250                 255

Pro Gly Xaa Gly Val Pro Gly Xaa Gly Val Pro Gly Xaa Gly Val Pro
            260                 265                 270

Gly Xaa Gly Val Pro Gly Xaa Gly Val Pro Gly Xaa Gly Val Pro Gly
        275                 280                 285

Xaa Gly Val Pro Gly Xaa Gly Val Pro Gly Xaa Gly Val Pro Gly Xaa
    290                 295                 300

Gly Val Pro Gly Xaa Gly Val Pro Gly Xaa Gly Val Pro Gly Xaa Gly
305                 310                 315                 320

Val Pro Gly Xaa Gly Val Pro Gly Xaa Gly Val Pro Gly Xaa Gly Val
                325                 330                 335

Pro Gly Xaa Gly Val Pro Gly Xaa Gly Val Pro Gly Xaa Gly Val Pro
            340                 345                 350

Gly Xaa Gly Val Pro Gly Xaa Gly Val Pro Gly Xaa Gly Val Pro Gly
        355                 360                 365

Xaa Gly Val Pro Gly Xaa Gly Val Pro Gly Xaa Gly Val Pro Gly Xaa
    370                 375                 380

Gly Val Pro Gly Xaa Gly Val Pro Gly Xaa Gly Val Pro Gly Xaa Gly
385                 390                 395                 400

Val Pro Gly Xaa Gly Val Pro Gly Xaa Gly Val Pro Gly Xaa Gly Val
                405                 410                 415

Pro Gly Xaa Gly Val Pro Gly Xaa Gly Val Pro Gly Xaa Gly Val Pro
            420                 425                 430

Gly Xaa Gly Val Pro Gly Xaa Gly Val Pro Gly Xaa Gly Val Pro Gly
        435                 440                 445

Xaa Gly
    450

<210> SEQ ID NO 14
<211> LENGTH: 600
<212> TYPE: PRT
<213> ORGANISM: Artificial Sequence
<220> FEATURE:
<223> OTHER INFORMATION: ELP biopolymer sequence
<220> FEATURE:
<221> NAME/KEY: misc_feature
<222> LOCATION: (4)..(4)
<223> OTHER INFORMATION: Xaa can be any naturally occurring or non-
      natural amino acid
<220> FEATURE:
<221> NAME/KEY: misc_feature
<222> LOCATION: (9)..(9)
<223> OTHER INFORMATION: Xaa can be any naturally occurring or non-
      natural amino acid
```

```
<220> FEATURE:
<221> NAME/KEY: misc_feature
<222> LOCATION: (14)..(14)
<223> OTHER INFORMATION: Xaa can be any naturally occurring or non-
      natural amino acid
<220> FEATURE:
<221> NAME/KEY: misc_feature
<222> LOCATION: (19)..(19)
<223> OTHER INFORMATION: Xaa can be any naturally occurring or non-
      natural amino acid
<220> FEATURE:
<221> NAME/KEY: misc_feature
<222> LOCATION: (24)..(24)
<223> OTHER INFORMATION: Xaa can be any naturally occurring or non-
      natural amino acid
<220> FEATURE:
<221> NAME/KEY: misc_feature
<222> LOCATION: (29)..(29)
<223> OTHER INFORMATION: Xaa can be any naturally occurring or non-
      natural amino acid
<220> FEATURE:
<221> NAME/KEY: misc_feature
<222> LOCATION: (34)..(34)
<223> OTHER INFORMATION: Xaa can be any naturally occurring or non-
      natural amino acid
<220> FEATURE:
<221> NAME/KEY: misc_feature
<222> LOCATION: (39)..(39)
<223> OTHER INFORMATION: Xaa can be any naturally occurring or non-
      natural amino acid
<220> FEATURE:
<221> NAME/KEY: misc_feature
<222> LOCATION: (44)..(44)
<223> OTHER INFORMATION: Xaa can be any naturally occurring or non-
      natural amino acid
<220> FEATURE:
<221> NAME/KEY: misc_feature
<222> LOCATION: (49)..(49)
<223> OTHER INFORMATION: Xaa can be any naturally occurring or non-
      natural amino acid
<220> FEATURE:
<221> NAME/KEY: misc_feature
<222> LOCATION: (54)..(54)
<223> OTHER INFORMATION: Xaa can be any naturally occurring or non-
      natural amino acid
<220> FEATURE:
<221> NAME/KEY: misc_feature
<222> LOCATION: (59)..(59)
<223> OTHER INFORMATION: Xaa can be any naturally occurring or non-
      natural amino acid
<220> FEATURE:
<221> NAME/KEY: misc_feature
<222> LOCATION: (64)..(64)
<223> OTHER INFORMATION: Xaa can be any naturally occurring or non-
      natural amino acid
<220> FEATURE:
<221> NAME/KEY: misc_feature
<222> LOCATION: (69)..(69)
<223> OTHER INFORMATION: Xaa can be any naturally occurring or non-
      natural amino acid
<220> FEATURE:
<221> NAME/KEY: misc_feature
<222> LOCATION: (74)..(74)
<223> OTHER INFORMATION: Xaa can be any naturally occurring or non-
      natural amino acid
<220> FEATURE:
<221> NAME/KEY: misc_feature
<222> LOCATION: (79)..(79)
<223> OTHER INFORMATION: Xaa can be any naturally occurring or non-
      natural amino acid
<220> FEATURE:
<221> NAME/KEY: misc_feature
<222> LOCATION: (84)..(84)
<223> OTHER INFORMATION: Xaa can be any naturally occurring or non-
      natural amino acid
<220> FEATURE:
<221> NAME/KEY: misc_feature
<222> LOCATION: (89)..(89)
<223> OTHER INFORMATION: Xaa can be any naturally occurring or non-
```

```
              natural amino acid
<220> FEATURE:
<221> NAME/KEY: misc_feature
<222> LOCATION: (94)..(94)
<223> OTHER INFORMATION: Xaa can be any naturally occurring or non-
              natural amino acid
<220> FEATURE:
<221> NAME/KEY: misc_feature
<222> LOCATION: (99)..(99)
<223> OTHER INFORMATION: Xaa can be any naturally occurring or non-
              natural amino acid
<220> FEATURE:
<221> NAME/KEY: misc_feature
<222> LOCATION: (104)..(104)
<223> OTHER INFORMATION: Xaa can be any naturally occurring or non-
              natural amino acid
<220> FEATURE:
<221> NAME/KEY: misc_feature
<222> LOCATION: (109)..(109)
<223> OTHER INFORMATION: Xaa can be any naturally occurring or non-
              natural amino acid
<220> FEATURE:
<221> NAME/KEY: misc_feature
<222> LOCATION: (114)..(114)
<223> OTHER INFORMATION: Xaa can be any naturally occurring or non-
              natural amino acid
<220> FEATURE:
<221> NAME/KEY: misc_feature
<222> LOCATION: (119)..(119)
<223> OTHER INFORMATION: Xaa can be any naturally occurring or non-
              natural amino acid
<220> FEATURE:
<221> NAME/KEY: misc_feature
<222> LOCATION: (124)..(124)
<223> OTHER INFORMATION: Xaa can be any naturally occurring or non-
              natural amino acid
<220> FEATURE:
<221> NAME/KEY: misc_feature
<222> LOCATION: (129)..(129)
<223> OTHER INFORMATION: Xaa can be any naturally occurring or non-
              natural amino acid
<220> FEATURE:
<221> NAME/KEY: misc_feature
<222> LOCATION: (134)..(134)
<223> OTHER INFORMATION: Xaa can be any naturally occurring or non-
              natural amino acid
<220> FEATURE:
<221> NAME/KEY: misc_feature
<222> LOCATION: (139)..(139)
<223> OTHER INFORMATION: Xaa can be any naturally occurring or non-
              natural amino acid
<220> FEATURE:
<221> NAME/KEY: misc_feature
<222> LOCATION: (144)..(144)
<223> OTHER INFORMATION: Xaa can be any naturally occurring or non-
              natural amino acid
<220> FEATURE:
<221> NAME/KEY: misc_feature
<222> LOCATION: (149)..(149)
<223> OTHER INFORMATION: Xaa can be any naturally occurring or non-
              natural amino acid
<220> FEATURE:
<221> NAME/KEY: misc_feature
<222> LOCATION: (154)..(154)
<223> OTHER INFORMATION: Xaa can be any naturally occurring or non-
              natural amino acid
<220> FEATURE:
<221> NAME/KEY: misc_feature
<222> LOCATION: (159)..(159)
<223> OTHER INFORMATION: Xaa can be any naturally occurring or non-
              natural amino acid
<220> FEATURE:
<221> NAME/KEY: misc_feature
<222> LOCATION: (164)..(164)
<223> OTHER INFORMATION: Xaa can be any naturally occurring or non-
              natural amino acid
<220> FEATURE:
<221> NAME/KEY: misc_feature
<222> LOCATION: (169)..(169)
```

```
<223> OTHER INFORMATION: Xaa can be any naturally occurring or non-
      natural amino acid
<220> FEATURE:
<221> NAME/KEY: misc_feature
<222> LOCATION: (174)..(174)
<223> OTHER INFORMATION: Xaa can be any naturally occurring or non-
      natural amino acid
<220> FEATURE:
<221> NAME/KEY: misc_feature
<222> LOCATION: (179)..(179)
<223> OTHER INFORMATION: Xaa can be any naturally occurring or non-
      natural amino acid
<220> FEATURE:
<221> NAME/KEY: misc_feature
<222> LOCATION: (184)..(184)
<223> OTHER INFORMATION: Xaa can be any naturally occurring or non-
      natural amino acid
<220> FEATURE:
<221> NAME/KEY: misc_feature
<222> LOCATION: (189)..(189)
<223> OTHER INFORMATION: Xaa can be any naturally occurring or non-
      natural amino acid
<220> FEATURE:
<221> NAME/KEY: misc_feature
<222> LOCATION: (194)..(194)
<223> OTHER INFORMATION: Xaa can be any naturally occurring or non-
      natural amino acid
<220> FEATURE:
<221> NAME/KEY: misc_feature
<222> LOCATION: (199)..(199)
<223> OTHER INFORMATION: Xaa can be any naturally occurring or non-
      natural amino acid
<220> FEATURE:
<221> NAME/KEY: misc_feature
<222> LOCATION: (204)..(204)
<223> OTHER INFORMATION: Xaa can be any naturally occurring or non-
      natural amino acid
<220> FEATURE:
<221> NAME/KEY: misc_feature
<222> LOCATION: (209)..(209)
<223> OTHER INFORMATION: Xaa can be any naturally occurring or non-
      natural amino acid
<220> FEATURE:
<221> NAME/KEY: misc_feature
<222> LOCATION: (214)..(214)
<223> OTHER INFORMATION: Xaa can be any naturally occurring or non-
      natural amino acid
<220> FEATURE:
<221> NAME/KEY: misc_feature
<222> LOCATION: (219)..(219)
<223> OTHER INFORMATION: Xaa can be any naturally occurring or non-
      natural amino acid
<220> FEATURE:
<221> NAME/KEY: misc_feature
<222> LOCATION: (224)..(224)
<223> OTHER INFORMATION: Xaa can be any naturally occurring or non-
      natural amino acid
<220> FEATURE:
<221> NAME/KEY: misc_feature
<222> LOCATION: (229)..(229)
<223> OTHER INFORMATION: Xaa can be any naturally occurring or non-
      natural amino acid
<220> FEATURE:
<221> NAME/KEY: misc_feature
<222> LOCATION: (234)..(234)
<223> OTHER INFORMATION: Xaa can be any naturally occurring or non-
      natural amino acid
<220> FEATURE:
<221> NAME/KEY: misc_feature
<222> LOCATION: (239)..(239)
<223> OTHER INFORMATION: Xaa can be any naturally occurring or non-
      natural amino acid
<220> FEATURE:
<221> NAME/KEY: misc_feature
<222> LOCATION: (244)..(244)
<223> OTHER INFORMATION: Xaa can be any naturally occurring or non-
      natural amino acid
<220> FEATURE:
<221> NAME/KEY: misc_feature
```

```
<222> LOCATION: (249)..(249)
<223> OTHER INFORMATION: Xaa can be any naturally occurring or non-
      natural amino acid
<220> FEATURE:
<221> NAME/KEY: misc_feature
<222> LOCATION: (254)..(254)
<223> OTHER INFORMATION: Xaa can be any naturally occurring or non-
      natural amino acid
<220> FEATURE:
<221> NAME/KEY: misc_feature
<222> LOCATION: (259)..(259)
<223> OTHER INFORMATION: Xaa can be any naturally occurring or non-
      natural amino acid
<220> FEATURE:
<221> NAME/KEY: misc_feature
<222> LOCATION: (264)..(264)
<223> OTHER INFORMATION: Xaa can be any naturally occurring or non-
      natural amino acid
<220> FEATURE:
<221> NAME/KEY: misc_feature
<222> LOCATION: (269)..(269)
<223> OTHER INFORMATION: Xaa can be any naturally occurring or non-
      natural amino acid
<220> FEATURE:
<221> NAME/KEY: misc_feature
<222> LOCATION: (274)..(274)
<223> OTHER INFORMATION: Xaa can be any naturally occurring or non-
      natural amino acid
<220> FEATURE:
<221> NAME/KEY: misc_feature
<222> LOCATION: (279)..(279)
<223> OTHER INFORMATION: Xaa can be any naturally occurring or non-
      natural amino acid
<220> FEATURE:
<221> NAME/KEY: misc_feature
<222> LOCATION: (284)..(284)
<223> OTHER INFORMATION: Xaa can be any naturally occurring or non-
      natural amino acid
<220> FEATURE:
<221> NAME/KEY: misc_feature
<222> LOCATION: (289)..(289)
<223> OTHER INFORMATION: Xaa can be any naturally occurring or non-
      natural amino acid
<220> FEATURE:
<221> NAME/KEY: misc_feature
<222> LOCATION: (294)..(294)
<223> OTHER INFORMATION: Xaa can be any naturally occurring or non-
      natural amino acid
<220> FEATURE:
<221> NAME/KEY: misc_feature
<222> LOCATION: (299)..(299)
<223> OTHER INFORMATION: Xaa can be any naturally occurring or non-
      natural amino acid
<220> FEATURE:
<221> NAME/KEY: misc_feature
<222> LOCATION: (304)..(304)
<223> OTHER INFORMATION: Xaa can be any naturally occurring or non-
      natural amino acid
<220> FEATURE:
<221> NAME/KEY: misc_feature
<222> LOCATION: (309)..(309)
<223> OTHER INFORMATION: Xaa can be any naturally occurring or non-
      natural amino acid
<220> FEATURE:
<221> NAME/KEY: misc_feature
<222> LOCATION: (314)..(314)
<223> OTHER INFORMATION: Xaa can be any naturally occurring or non-
      natural amino acid
<220> FEATURE:
<221> NAME/KEY: misc_feature
<222> LOCATION: (319)..(319)
<223> OTHER INFORMATION: Xaa can be any naturally occurring or non-
      natural amino acid
<220> FEATURE:
<221> NAME/KEY: misc_feature
<222> LOCATION: (324)..(324)
<223> OTHER INFORMATION: Xaa can be any naturally occurring or non-
      natural amino acid
<220> FEATURE:
```

```
<221> NAME/KEY: misc_feature
<222> LOCATION: (329)..(329)
<223> OTHER INFORMATION: Xaa can be any naturally occurring or non-
      natural amino acid
<220> FEATURE:
<221> NAME/KEY: misc_feature
<222> LOCATION: (334)..(334)
<223> OTHER INFORMATION: Xaa can be any naturally occurring or non-
      natural amino acid
<220> FEATURE:
<221> NAME/KEY: misc_feature
<222> LOCATION: (339)..(339)
<223> OTHER INFORMATION: Xaa can be any naturally occurring or non-
      natural amino acid
<220> FEATURE:
<221> NAME/KEY: misc_feature
<222> LOCATION: (344)..(344)
<223> OTHER INFORMATION: Xaa can be any naturally occurring or non-
      natural amino acid
<220> FEATURE:
<221> NAME/KEY: misc_feature
<222> LOCATION: (349)..(349)
<223> OTHER INFORMATION: Xaa can be any naturally occurring or non-
      natural amino acid
<220> FEATURE:
<221> NAME/KEY: misc_feature
<222> LOCATION: (354)..(354)
<223> OTHER INFORMATION: Xaa can be any naturally occurring or non-
      natural amino acid
<220> FEATURE:
<221> NAME/KEY: misc_feature
<222> LOCATION: (359)..(359)
<223> OTHER INFORMATION: Xaa can be any naturally occurring or non-
      natural amino acid
<220> FEATURE:
<221> NAME/KEY: misc_feature
<222> LOCATION: (364)..(364)
<223> OTHER INFORMATION: Xaa can be any naturally occurring or non-
      natural amino acid
<220> FEATURE:
<221> NAME/KEY: misc_feature
<222> LOCATION: (369)..(369)
<223> OTHER INFORMATION: Xaa can be any naturally occurring or non-
      natural amino acid
<220> FEATURE:
<221> NAME/KEY: misc_feature
<222> LOCATION: (374)..(374)
<223> OTHER INFORMATION: Xaa can be any naturally occurring or non-
      natural amino acid
<220> FEATURE:
<221> NAME/KEY: misc_feature
<222> LOCATION: (379)..(379)
<223> OTHER INFORMATION: Xaa can be any naturally occurring or non-
      natural amino acid
<220> FEATURE:
<221> NAME/KEY: misc_feature
<222> LOCATION: (384)..(384)
<223> OTHER INFORMATION: Xaa can be any naturally occurring or non-
      natural amino acid
<220> FEATURE:
<221> NAME/KEY: misc_feature
<222> LOCATION: (389)..(389)
<223> OTHER INFORMATION: Xaa can be any naturally occurring or non-
      natural amino acid
<220> FEATURE:
<221> NAME/KEY: misc_feature
<222> LOCATION: (394)..(394)
<223> OTHER INFORMATION: Xaa can be any naturally occurring or non-
      natural amino acid
<220> FEATURE:
<221> NAME/KEY: misc_feature
<222> LOCATION: (399)..(399)
<223> OTHER INFORMATION: Xaa can be any naturally occurring or non-
      natural amino acid
<220> FEATURE:
<221> NAME/KEY: misc_feature
<222> LOCATION: (404)..(404)
<223> OTHER INFORMATION: Xaa can be any naturally occurring or non-
      natural amino acid
```

```
<220> FEATURE:
<221> NAME/KEY: misc_feature
<222> LOCATION: (409)..(409)
<223> OTHER INFORMATION: Xaa can be any naturally occurring or non-
      natural amino acid
<220> FEATURE:
<221> NAME/KEY: misc_feature
<222> LOCATION: (414)..(414)
<223> OTHER INFORMATION: Xaa can be any naturally occurring or non-
      natural amino acid
<220> FEATURE:
<221> NAME/KEY: misc_feature
<222> LOCATION: (419)..(419)
<223> OTHER INFORMATION: Xaa can be any naturally occurring or non-
      natural amino acid
<220> FEATURE:
<221> NAME/KEY: misc_feature
<222> LOCATION: (424)..(424)
<223> OTHER INFORMATION: Xaa can be any naturally occurring or non-
      natural amino acid
<220> FEATURE:
<221> NAME/KEY: misc_feature
<222> LOCATION: (429)..(429)
<223> OTHER INFORMATION: Xaa can be any naturally occurring or non-
      natural amino acid
<220> FEATURE:
<221> NAME/KEY: misc_feature
<222> LOCATION: (434)..(434)
<223> OTHER INFORMATION: Xaa can be any naturally occurring or non-
      natural amino acid
<220> FEATURE:
<221> NAME/KEY: misc_feature
<222> LOCATION: (439)..(439)
<223> OTHER INFORMATION: Xaa can be any naturally occurring or non-
      natural amino acid
<220> FEATURE:
<221> NAME/KEY: misc_feature
<222> LOCATION: (444)..(444)
<223> OTHER INFORMATION: Xaa can be any naturally occurring or non-
      natural amino acid
<220> FEATURE:
<221> NAME/KEY: misc_feature
<222> LOCATION: (449)..(449)
<223> OTHER INFORMATION: Xaa can be any naturally occurring or non-
      natural amino acid
<220> FEATURE:
<221> NAME/KEY: misc_feature
<222> LOCATION: (454)..(454)
<223> OTHER INFORMATION: Xaa can be any naturally occurring or non-
      natural amino acid
<220> FEATURE:
<221> NAME/KEY: misc_feature
<222> LOCATION: (459)..(459)
<223> OTHER INFORMATION: Xaa can be any naturally occurring or non-
      natural amino acid
<220> FEATURE:
<221> NAME/KEY: misc_feature
<222> LOCATION: (464)..(464)
<223> OTHER INFORMATION: Xaa can be any naturally occurring or non-
      natural amino acid
<220> FEATURE:
<221> NAME/KEY: misc_feature
<222> LOCATION: (469)..(469)
<223> OTHER INFORMATION: Xaa can be any naturally occurring or non-
      natural amino acid
<220> FEATURE:
<221> NAME/KEY: misc_feature
<222> LOCATION: (474)..(474)
<223> OTHER INFORMATION: Xaa can be any naturally occurring or non-
      natural amino acid
<220> FEATURE:
<221> NAME/KEY: misc_feature
<222> LOCATION: (479)..(479)
<223> OTHER INFORMATION: Xaa can be any naturally occurring or non-
      natural amino acid
<220> FEATURE:
<221> NAME/KEY: misc_feature
<222> LOCATION: (484)..(484)
<223> OTHER INFORMATION: Xaa can be any naturally occurring or non-
```

```
      natural amino acid
<220> FEATURE:
<221> NAME/KEY: misc_feature
<222> LOCATION: (489)..(489)
<223> OTHER INFORMATION: Xaa can be any naturally occurring or non-
      natural amino acid
<220> FEATURE:
<221> NAME/KEY: misc_feature
<222> LOCATION: (494)..(494)
<223> OTHER INFORMATION: Xaa can be any naturally occurring or non-
      natural amino acid
<220> FEATURE:
<221> NAME/KEY: misc_feature
<222> LOCATION: (499)..(499)
<223> OTHER INFORMATION: Xaa can be any naturally occurring or non-
      natural amino acid
<220> FEATURE:
<221> NAME/KEY: misc_feature
<222> LOCATION: (504)..(504)
<223> OTHER INFORMATION: Xaa can be any naturally occurring or non-
      natural amino acid
<220> FEATURE:
<221> NAME/KEY: misc_feature
<222> LOCATION: (509)..(509)
<223> OTHER INFORMATION: Xaa can be any naturally occurring or non-
      natural amino acid
<220> FEATURE:
<221> NAME/KEY: misc_feature
<222> LOCATION: (514)..(514)
<223> OTHER INFORMATION: Xaa can be any naturally occurring or non-
      natural amino acid
<220> FEATURE:
<221> NAME/KEY: misc_feature
<222> LOCATION: (519)..(519)
<223> OTHER INFORMATION: Xaa can be any naturally occurring or non-
      natural amino acid
<220> FEATURE:
<221> NAME/KEY: misc_feature
<222> LOCATION: (524)..(524)
<223> OTHER INFORMATION: Xaa can be any naturally occurring or non-
      natural amino acid
<220> FEATURE:
<221> NAME/KEY: misc_feature
<222> LOCATION: (529)..(529)
<223> OTHER INFORMATION: Xaa can be any naturally occurring or non-
      natural amino acid
<220> FEATURE:
<221> NAME/KEY: misc_feature
<222> LOCATION: (534)..(534)
<223> OTHER INFORMATION: Xaa can be any naturally occurring or non-
      natural amino acid
<220> FEATURE:
<221> NAME/KEY: misc_feature
<222> LOCATION: (539)..(539)
<223> OTHER INFORMATION: Xaa can be any naturally occurring or non-
      natural amino acid
<220> FEATURE:
<221> NAME/KEY: misc_feature
<222> LOCATION: (544)..(544)
<223> OTHER INFORMATION: Xaa can be any naturally occurring or non-
      natural amino acid
<220> FEATURE:
<221> NAME/KEY: misc_feature
<222> LOCATION: (549)..(549)
<223> OTHER INFORMATION: Xaa can be any naturally occurring or non-
      natural amino acid
<220> FEATURE:
<221> NAME/KEY: misc_feature
<222> LOCATION: (554)..(554)
<223> OTHER INFORMATION: Xaa can be any naturally occurring or non-
      natural amino acid
<220> FEATURE:
<221> NAME/KEY: misc_feature
<222> LOCATION: (559)..(559)
<223> OTHER INFORMATION: Xaa can be any naturally occurring or non-
      natural amino acid
<220> FEATURE:
<221> NAME/KEY: misc_feature
<222> LOCATION: (564)..(564)
```

<223> OTHER INFORMATION: Xaa can be any naturally occurring or non-
      natural amino acid
<220> FEATURE:
<221> NAME/KEY: misc_feature
<222> LOCATION: (569)..(569)
<223> OTHER INFORMATION: Xaa can be any naturally occurring or non-
      natural amino acid
<220> FEATURE:
<221> NAME/KEY: misc_feature
<222> LOCATION: (574)..(574)
<223> OTHER INFORMATION: Xaa can be any naturally occurring or non-
      natural amino acid
<220> FEATURE:
<221> NAME/KEY: misc_feature
<222> LOCATION: (579)..(579)
<223> OTHER INFORMATION: Xaa can be any naturally occurring or non-
      natural amino acid
<220> FEATURE:
<221> NAME/KEY: misc_feature
<222> LOCATION: (584)..(584)
<223> OTHER INFORMATION: Xaa can be any naturally occurring or non-
      natural amino acid
<220> FEATURE:
<221> NAME/KEY: misc_feature
<222> LOCATION: (589)..(589)
<223> OTHER INFORMATION: Xaa can be any naturally occurring or non-
      natural amino acid
<220> FEATURE:
<221> NAME/KEY: misc_feature
<222> LOCATION: (594)..(594)
<223> OTHER INFORMATION: Xaa can be any naturally occurring or non-
      natural amino acid
<220> FEATURE:
<221> NAME/KEY: misc_feature
<222> LOCATION: (599)..(599)
<223> OTHER INFORMATION: Xaa can be any naturally occurring or non-
      natural amino acid

<400> SEQUENCE: 14

Val Pro Gly Xaa Gly Val Pro Gly Xaa Gly Val Pro Gly Xaa Gly Val
1               5                   10                  15

Pro Gly Xaa Gly Val Pro Gly Xaa Gly Val Pro Gly Xaa Gly Val Pro
            20                  25                  30

Gly Xaa Gly Val Pro Gly Xaa Gly Val Pro Gly Xaa Gly Val Pro Gly
        35                  40                  45

Xaa Gly Val Pro Gly Xaa Gly Val Pro Gly Xaa Gly Val Pro Gly Xaa
    50                  55                  60

Gly Val Pro Gly Xaa Gly Val Pro Gly Xaa Gly Val Pro Gly Xaa Gly
65                  70                  75                  80

Val Pro Gly Xaa Gly Val Pro Gly Xaa Gly Val Pro Gly Xaa Gly Val
                85                  90                  95

Pro Gly Xaa Gly Val Pro Gly Xaa Gly Val Pro Gly Xaa Gly Val Pro
            100                 105                 110

Gly Xaa Gly Val Pro Gly Xaa Gly Val Pro Gly Xaa Gly Val Pro Gly
        115                 120                 125

Xaa Gly Val Pro Gly Xaa Gly Val Pro Gly Xaa Gly Val Pro Gly Xaa
    130                 135                 140

Gly Val Pro Gly Xaa Gly Val Pro Gly Xaa Gly Val Pro Gly Xaa Gly
145                 150                 155                 160

Val Pro Gly Xaa Gly Val Pro Gly Xaa Gly Val Pro Gly Xaa Gly Val
                165                 170                 175

Pro Gly Xaa Gly Val Pro Gly Xaa Gly Val Pro Gly Xaa Gly Val Pro
            180                 185                 190

Gly Xaa Gly Val Pro Gly Xaa Gly Val Pro Gly Xaa Gly Val Pro Gly
        195                 200                 205

Xaa Gly Val Pro Gly Xaa Gly Val Pro Gly Xaa Gly Val Pro Gly Xaa
    210                 215                 220

Gly Val Pro Gly Xaa Gly Val Pro Gly Xaa Gly Val Pro Gly Xaa Gly
225                 230                 235                 240

Val Pro Gly Xaa Gly Val Pro Gly Xaa Gly Val Pro Gly Xaa Gly Val
            245                 250                 255

Pro Gly Xaa Gly Val Pro Gly Xaa Gly Val Pro Gly Xaa Gly Val Pro
        260                 265                 270

Gly Xaa Gly Val Pro Gly Xaa Gly Val Pro Gly Xaa Gly Val Pro Gly
    275                 280                 285

Xaa Gly Val Pro Gly Xaa Gly Val Pro Gly Xaa Gly Val Pro Gly Xaa
    290                 295                 300

Gly Val Pro Gly Xaa Gly Val Pro Gly Xaa Gly Val Pro Gly Xaa Gly
305                 310                 315                 320

Val Pro Gly Xaa Gly Val Pro Gly Xaa Gly Val Pro Gly Xaa Gly Val
            325                 330                 335

Pro Gly Xaa Gly Val Pro Gly Xaa Gly Val Pro Gly Xaa Gly Val Pro
        340                 345                 350

Gly Xaa Gly Val Pro Gly Xaa Gly Val Pro Gly Xaa Gly Val Pro Gly
    355                 360                 365

Xaa Gly Val Pro Gly Xaa Gly Val Pro Gly Xaa Gly Val Pro Gly Xaa
    370                 375                 380

Gly Val Pro Gly Xaa Gly Val Pro Gly Xaa Gly Val Pro Gly Xaa Gly
385                 390                 395                 400

Val Pro Gly Xaa Gly Val Pro Gly Xaa Gly Val Pro Gly Xaa Gly Val
            405                 410                 415

Pro Gly Xaa Gly Val Pro Gly Xaa Gly Val Pro Gly Xaa Gly Val Pro
        420                 425                 430

Gly Xaa Gly Val Pro Gly Xaa Gly Val Pro Gly Xaa Gly Val Pro Gly
    435                 440                 445

Xaa Gly Val Pro Gly Xaa Gly Val Pro Gly Xaa Gly Val Pro Gly Xaa
    450                 455                 460

Gly Val Pro Gly Xaa Gly Val Pro Gly Xaa Gly Val Pro Gly Xaa Gly
465                 470                 475                 480

Val Pro Gly Xaa Gly Val Pro Gly Xaa Gly Val Pro Gly Xaa Gly Val
            485                 490                 495

Pro Gly Xaa Gly Val Pro Gly Xaa Gly Val Pro Gly Xaa Gly Val Pro
        500                 505                 510

Gly Xaa Gly Val Pro Gly Xaa Gly Val Pro Gly Xaa Gly Val Pro Gly
    515                 520                 525

Xaa Gly Val Pro Gly Xaa Gly Val Pro Gly Xaa Gly Val Pro Gly Xaa
    530                 535                 540

Gly Val Pro Gly Xaa Gly Val Pro Gly Xaa Gly Val Pro Gly Xaa Gly
545                 550                 555                 560

Val Pro Gly Xaa Gly Val Pro Gly Xaa Gly Val Pro Gly Xaa Gly Val
            565                 570                 575

Pro Gly Xaa Gly Val Pro Gly Xaa Gly Val Pro Gly Xaa Gly Val Pro
        580                 585                 590

Gly Xaa Gly Val Pro Gly Xaa Gly
    595                 600

<210> SEQ ID NO 15
<211> LENGTH: 450

<212> TYPE: PRT
<213> ORGANISM: Artificial Sequence
<220> FEATURE:
<223> OTHER INFORMATION: ELP biopolymer sequence

<400> SEQUENCE: 15

```
Val Pro Gly Val Gly Val Pro Gly Val Gly Val Pro Gly Val Gly Val
1               5                   10                  15

Pro Gly Val Gly Val Pro Gly Val Gly Val Pro Gly Val Gly Val Pro
            20                  25                  30

Gly Val Gly Val Pro Gly Val Gly Val Pro Gly Val Gly Val Pro Gly
        35                  40                  45

Val Gly Val Pro Gly Val Gly Val Pro Gly Val Gly Val Pro Gly Val
    50                  55                  60

Gly Val Pro Gly Val Gly Val Pro Gly Val Gly Val Pro Gly Val Gly
65                  70                  75                  80

Val Pro Gly Val Gly Val Pro Gly Val Gly Val Pro Gly Val Gly Val
                85                  90                  95

Pro Gly Val Gly Val Pro Gly Val Gly Val Pro Gly Val Gly Val Pro
            100                 105                 110

Gly Val Gly Val Pro Gly Val Gly Val Pro Gly Val Gly Val Pro Gly
        115                 120                 125

Val Gly Val Pro Gly Val Gly Val Pro Gly Val Gly Val Pro Gly Val
    130                 135                 140

Gly Val Pro Gly Val Gly Val Pro Gly Val Gly Val Pro Gly Val Gly
145                 150                 155                 160

Val Pro Gly Val Gly Val Pro Gly Val Gly Val Pro Gly Val Gly Val
                165                 170                 175

Pro Gly Val Gly Val Pro Gly Val Gly Val Pro Gly Val Gly Val Pro
            180                 185                 190

Gly Val Gly Val Pro Gly Val Gly Val Pro Gly Val Gly Val Pro Gly
        195                 200                 205

Val Gly Val Pro Gly Val Gly Val Pro Gly Val Gly Val Pro Gly Val
    210                 215                 220

Gly Val Pro Gly Val Gly Val Pro Gly Val Gly Val Pro Gly Val Gly
225                 230                 235                 240

Val Pro Gly Val Gly Val Pro Gly Val Gly Val Pro Gly Val Gly Val
                245                 250                 255

Pro Gly Val Gly Val Pro Gly Val Gly Val Pro Gly Val Gly Val Pro
            260                 265                 270

Gly Val Gly Val Pro Gly Val Gly Val Pro Gly Val Gly Val Pro Gly
        275                 280                 285

Val Gly Val Pro Gly Val Gly Val Pro Gly Val Gly Val Pro Gly Val
    290                 295                 300

Gly Val Pro Gly Val Gly Val Pro Gly Val Gly Val Pro Gly Val Gly
305                 310                 315                 320

Val Pro Gly Val Gly Val Pro Gly Val Gly Val Pro Gly Val Gly Val
                325                 330                 335

Pro Gly Val Gly Val Pro Gly Val Gly Val Pro Gly Val Gly Val Pro
            340                 345                 350

Gly Val Gly Val Pro Gly Val Gly Val Pro Gly Val Gly Val Pro Gly
        355                 360                 365

Val Gly Val Pro Gly Val Gly Val Pro Gly Val Gly Val Pro Gly Val
    370                 375                 380
```

```
Gly Val Pro Gly Val Gly Val Pro Gly Val Gly Val Pro Gly Val Gly
            385                 390                 395                 400

Val Pro Gly Val Gly Val Pro Gly Val Gly Val Pro Gly Val Gly Val
                405                 410                 415

Pro Gly Val Gly Val Pro Gly Val Gly Val Pro Gly Val Gly Val Pro
            420                 425                 430

Gly Val Gly Val Pro Gly Val Gly Val Pro Gly Val Gly Val Pro Gly
        435                 440                 445

Val Gly
    450

<210> SEQ ID NO 16
<211> LENGTH: 600
<212> TYPE: PRT
<213> ORGANISM: Artificial Sequence
<220> FEATURE:
<223> OTHER INFORMATION: ELP biopolymer sequence

<400> SEQUENCE: 16

Val Pro Gly Val Gly Val Pro Gly Val Gly Val Pro Gly Val Gly Val
1               5                   10                  15

Pro Gly Val Gly Val Pro Gly Val Gly Val Pro Gly Val Gly Val Pro
            20                  25                  30

Gly Val Gly Val Pro Gly Val Gly Val Pro Gly Val Gly Val Pro Gly
        35                  40                  45

Val Gly Val Pro Gly Val Gly Val Pro Gly Val Gly Val Pro Gly Val
    50                  55                  60

Gly Val Pro Gly Val Gly Val Pro Gly Val Gly Val Pro Gly Val Gly
65                  70                  75                  80

Val Pro Gly Val Gly Val Pro Gly Val Gly Val Pro Gly Val Gly Val
                85                  90                  95

Pro Gly Val Gly Val Pro Gly Val Gly Val Pro Gly Val Gly Val Pro
            100                 105                 110

Gly Val Gly Val Pro Gly Val Gly Val Pro Gly Val Gly Val Pro Gly
        115                 120                 125

Val Gly Val Pro Gly Val Gly Val Pro Gly Val Gly Val Pro Gly Val
    130                 135                 140

Gly Val Pro Gly Val Gly Val Pro Gly Val Gly Val Pro Gly Val Gly
145                 150                 155                 160

Val Pro Gly Val Gly Val Pro Gly Val Gly Val Pro Gly Val Gly Val
                165                 170                 175

Pro Gly Val Gly Val Pro Gly Val Gly Val Pro Gly Val Gly Val Pro
            180                 185                 190

Gly Val Gly Val Pro Gly Val Gly Val Pro Gly Val Gly Val Pro Gly
        195                 200                 205

Val Gly Val Pro Gly Val Gly Val Pro Gly Val Gly Val Pro Gly Val
    210                 215                 220

Gly Val Pro Gly Val Gly Val Pro Gly Val Gly Val Pro Gly Val Gly
225                 230                 235                 240

Val Pro Gly Val Gly Val Pro Gly Val Gly Val Pro Gly Val Gly Val
                245                 250                 255

Pro Gly Val Gly Val Pro Gly Val Gly Val Pro Gly Val Gly Val Pro
            260                 265                 270

Gly Val Gly Val Pro Gly Val Gly Val Pro Gly Val Gly Val Pro Gly
        275                 280                 285
```

Val Gly Val Pro Gly Val Gly Val Pro Gly Val Gly Val Pro Gly Val
        290                 295                 300

Gly Val Pro Gly Val Gly Val Pro Gly Val Gly Val Pro Gly Val Gly
305                 310                 315                 320

Val Pro Gly Val Gly Val Pro Gly Val Gly Val Pro Gly Val Gly Val
            325                 330                 335

Pro Gly Val Gly Val Pro Gly Val Gly Val Pro Gly Val Gly Val Pro
            340                 345                 350

Gly Val Gly Val Pro Gly Val Gly Val Pro Gly Val Gly Val Pro Gly
        355                 360                 365

Val Gly Val Pro Gly Val Gly Val Pro Gly Val Gly Val Pro Gly Val
    370                 375                 380

Gly Val Pro Gly Val Gly Val Pro Gly Val Gly Val Pro Gly Val Gly
385                 390                 395                 400

Val Pro Gly Val Gly Val Pro Gly Val Gly Val Pro Gly Val Gly Val
            405                 410                 415

Pro Gly Val Gly Val Pro Gly Val Gly Val Pro Gly Val Gly Val Pro
            420                 425                 430

Gly Val Gly Val Pro Gly Val Gly Val Pro Gly Val Gly Val Pro Gly
        435                 440                 445

Val Gly Val Pro Gly Val Gly Val Pro Gly Val Gly Val Pro Gly Val
    450                 455                 460

Gly Val Pro Gly Val Gly Val Pro Gly Val Gly Val Pro Gly Val Gly
465                 470                 475                 480

Val Pro Gly Val Gly Val Pro Gly Val Gly Val Pro Gly Val Gly Val
            485                 490                 495

Pro Gly Val Gly Val Pro Gly Val Gly Val Pro Gly Val Gly Val Pro
            500                 505                 510

Gly Val Gly Val Pro Gly Val Gly Val Pro Gly Val Gly Val Pro Gly
        515                 520                 525

Val Gly Val Pro Gly Val Gly Val Pro Gly Val Gly Val Pro Gly Val
    530                 535                 540

Gly Val Pro Gly Val Gly Val Pro Gly Val Gly Val Pro Gly Val Gly
545                 550                 555                 560

Val Pro Gly Val Gly Val Pro Gly Val Gly Val Pro Gly Val Gly Val
            565                 570                 575

Pro Gly Val Gly Val Pro Gly Val Gly Val Pro Gly Val Gly Val Pro
            580                 585                 590

Gly Val Gly Val Pro Gly Val Gly
        595                 600

<210> SEQ ID NO 17
<211> LENGTH: 30
<212> TYPE: PRT
<213> ORGANISM: Homo sapiens

<400> SEQUENCE: 17

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 18
<211> LENGTH: 39
<212> TYPE: PRT
<213> ORGANISM: Homo sapiens

```
<400> SEQUENCE: 18

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
35

<210> SEQ ID NO 19
<211> LENGTH: 37
<212> TYPE: PRT
<213> ORGANISM: Homo sapiens

<400> SEQUENCE: 19

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Lys Asn Asn Ile Ala
        35

<210> SEQ ID NO 20
<211> LENGTH: 29
<212> TYPE: PRT
<213> ORGANISM: Homo sapiens

<400> SEQUENCE: 20

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 21
<211> LENGTH: 33
<212> TYPE: PRT
<213> ORGANISM: Homo sapiens

<400> SEQUENCE: 21

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 22
<211> LENGTH: 29
<212> TYPE: PRT
<213> ORGANISM: Homo sapiens

<400> SEQUENCE: 22

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln
            20                  25

<210> SEQ ID NO 23
<211> LENGTH: 86
<212> TYPE: PRT
<213> ORGANISM: Homo sapiens
```

-continued

```
<400> SEQUENCE: 23

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85

<210> SEQ ID NO 24
<211> LENGTH: 691
<212> TYPE: PRT
<213> ORGANISM: Artificial Sequence
<220> FEATURE:
<223> OTHER INFORMATION: ELP-1-120 fusion protein

<400> SEQUENCE: 24

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn Val Pro Gly Val Gly Val Pro Gly Val Gly
                85                  90                  95

Val Pro Gly Gly Gly Val Pro Gly Ala Gly Val Pro Gly Val Gly Val
            100                 105                 110

Pro Gly Val Gly Val Pro Gly Val Gly Val Pro Gly Gly Gly Val Pro
        115                 120                 125

Gly Ala Gly Val Pro Gly Gly Val Pro Gly Val Gly Val Pro Gly
    130                 135                 140

Val Gly Val Pro Gly Gly Gly Val Pro Gly Ala Gly Val Pro Gly Val
145                 150                 155                 160

Gly Val Pro Gly Val Gly Val Pro Gly Val Gly Val Pro Gly Gly Gly
                165                 170                 175

Val Pro Gly Ala Gly Val Pro Gly Gly Gly Val Pro Gly Val Gly Val
            180                 185                 190

Pro Gly Val Gly Val Pro Gly Gly Val Pro Gly Ala Gly Val Pro
        195                 200                 205

Gly Val Gly Val Pro Gly Val Gly Val Pro Gly Val Gly Val Pro Gly
    210                 215                 220

Gly Gly Val Pro Gly Ala Gly Val Pro Gly Gly Gly Val Pro Gly Val
225                 230                 235                 240

Gly Val Pro Gly Val Gly Val Pro Gly Gly Gly Val Pro Gly Ala Gly
                245                 250                 255

Val Pro Gly Val Gly Val Pro Gly Val Gly Val Pro Gly Val Gly Val
```

```
                260                 265                 270
Pro Gly Gly Gly Val Pro Gly Ala Gly Val Pro Gly Gly Gly Val Pro
            275                 280                 285
Gly Val Gly Val Pro Gly Val Gly Val Pro Gly Gly Gly Val Pro Gly
        290                 295                 300
Ala Gly Val Pro Gly Val Gly Val Pro Gly Val Gly Val Pro Gly Val
305                 310                 315                 320
Gly Val Pro Gly Gly Val Pro Gly Ala Gly Val Pro Gly Gly Gly
                325                 330                 335
Val Pro Gly Val Gly Val Pro Gly Val Gly Val Pro Gly Gly Gly Val
            340                 345                 350
Pro Gly Ala Gly Val Pro Gly Val Gly Val Pro Gly Val Gly Val Pro
        355                 360                 365
Gly Val Gly Val Pro Gly Gly Val Pro Gly Ala Gly Val Pro Gly
370                 375                 380
Gly Gly Val Pro Gly Val Gly Val Pro Gly Val Gly Val Pro Gly Gly
385                 390                 395                 400
Gly Val Pro Gly Ala Gly Val Pro Gly Val Gly Val Pro Gly Val Gly
                405                 410                 415
Val Pro Gly Val Gly Val Pro Gly Gly Gly Val Pro Gly Ala Gly Val
            420                 425                 430
Pro Gly Gly Gly Val Pro Gly Val Gly Val Pro Gly Val Gly Val Pro
        435                 440                 445
Gly Gly Gly Val Pro Gly Ala Gly Val Pro Gly Val Gly Val Pro Gly
    450                 455                 460
Val Gly Val Pro Gly Val Gly Val Pro Gly Gly Gly Val Pro Gly Ala
465                 470                 475                 480
Gly Val Pro Gly Gly Gly Val Pro Gly Val Gly Val Pro Gly Val Gly
                485                 490                 495
Val Pro Gly Gly Gly Val Pro Gly Ala Gly Val Pro Gly Val Gly Val
            500                 505                 510
Pro Gly Val Gly Val Pro Gly Val Gly Val Pro Gly Gly Gly Val Pro
        515                 520                 525
Gly Ala Gly Val Pro Gly Gly Gly Val Pro Gly Val Gly Val Pro Gly
    530                 535                 540
Val Gly Val Pro Gly Gly Gly Val Pro Gly Ala Gly Val Pro Gly Val
545                 550                 555                 560
Gly Val Pro Gly Val Gly Val Pro Gly Val Gly Val Pro Gly Gly Gly
                565                 570                 575
Val Pro Gly Ala Gly Val Pro Gly Gly Gly Val Pro Gly Val Gly Val
            580                 585                 590
Pro Gly Val Gly Val Pro Gly Gly Gly Val Pro Gly Ala Gly Val Pro
        595                 600                 605
Gly Val Gly Val Pro Gly Val Gly Val Pro Gly Val Gly Val Pro Gly
    610                 615                 620
Gly Gly Val Pro Gly Ala Gly Val Pro Gly Gly Gly Val Pro Gly Val
625                 630                 635                 640
Gly Val Pro Gly Val Gly Val Pro Gly Gly Gly Val Pro Gly Ala Gly
                645                 650                 655
Val Pro Gly Val Gly Val Pro Gly Val Gly Val Pro Gly Val Gly Val
            660                 665                 670
Pro Gly Gly Gly Val Pro Gly Ala Gly Val Pro Gly Gly Gly Val Pro
        675                 680                 685
```

-continued

Gly Trp Pro
    690

<210> SEQ ID NO 25
<211> LENGTH: 636
<212> TYPE: PRT
<213> ORGANISM: Artificial Sequence
<220> FEATURE:
<223> OTHER INFORMATION: GLP-1/ELP fusion protein

<400> SEQUENCE: 25

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Val
            20                  25                  30

Pro Gly Val Gly Val Pro Gly Val Gly Val Pro Gly Gly Gly Val Pro
        35                  40                  45

Gly Ala Gly Val Pro Gly Val Gly Val Pro Gly Val Gly Val Pro Gly
    50                  55                  60

Val Gly Val Pro Gly Gly Val Pro Gly Ala Gly Val Pro Gly Gly
65                  70                  75                  80

Gly Val Pro Gly Val Gly Val Pro Gly Val Gly Val Pro Gly Gly Gly
                85                  90                  95

Val Pro Gly Ala Gly Val Pro Gly Val Gly Val Pro Gly Val Gly Val
            100                 105                 110

Pro Gly Gly Gly Val Pro Gly Gly Gly Val Pro Gly Ala Gly Val Pro
        115                 120                 125

Gly Gly Gly Val Pro Gly Val Gly Val Pro Gly Val Gly Val Pro Gly
    130                 135                 140

Gly Gly Val Pro Gly Ala Gly Val Pro Gly Gly Gly Val Pro Gly Val
145                 150                 155                 160

Gly Val Pro Gly Val Gly Val Pro Gly Gly Gly Val Pro Gly Ala Gly
                165                 170                 175

Val Pro Gly Gly Gly Val Pro Gly Val Gly Val Pro Gly Val Gly Val
            180                 185                 190

Pro Gly Gly Gly Val Pro Gly Ala Gly Val Pro Gly Val Gly Val Pro
        195                 200                 205

Gly Val Gly Val Pro Gly Val Gly Val Pro Gly Gly Gly Val Pro Gly
    210                 215                 220

Ala Gly Val Pro Gly Gly Gly Val Pro Gly Val Gly Val Pro Gly Val
225                 230                 235                 240

Gly Val Pro Gly Gly Gly Val Pro Gly Ala Gly Val Pro Gly Val Gly
                245                 250                 255

Val Pro Gly Val Gly Val Pro Gly Val Gly Val Pro Gly Gly Gly Val
            260                 265                 270

Pro Gly Ala Gly Val Pro Gly Gly Gly Val Pro Gly Val Gly Val Pro
        275                 280                 285

Gly Val Gly Val Pro Gly Gly Gly Val Pro Gly Ala Gly Val Pro Gly
    290                 295                 300

Val Gly Val Pro Gly Val Gly Val Pro Gly Val Gly Val Pro Gly Gly
305                 310                 315                 320

Gly Val Pro Gly Ala Gly Val Pro Gly Gly Gly Val Pro Gly Val Gly
                325                 330                 335

Val Pro Gly Val Gly Val Pro Gly Gly Gly Val Pro Gly Ala Gly Val
            340                 345                 350

```
Pro Gly Val Gly Val Pro Gly Val Gly Val Pro Gly Val Gly Val Pro
        355                 360                 365
Gly Gly Gly Val Pro Gly Ala Gly Val Pro Gly Gly Gly Val Pro Gly
        370                 375                 380
Val Gly Val Pro Gly Val Gly Val Pro Gly Gly Gly Val Pro Gly Ala
385                 390                 395                 400
Gly Val Pro Gly Val Gly Val Pro Gly Val Gly Val Pro Gly Val Gly
                405                 410                 415
Val Pro Gly Gly Gly Val Pro Gly Ala Gly Val Pro Gly Gly Gly Val
                420                 425                 430
Pro Gly Val Gly Val Pro Gly Val Gly Val Pro Gly Gly Gly Val Pro
        435                 440                 445
Gly Ala Gly Val Pro Gly Val Gly Val Pro Gly Val Gly Val Pro Gly
        450                 455                 460
Val Gly Val Pro Gly Gly Gly Val Pro Gly Ala Gly Val Pro Gly Gly
465                 470                 475                 480
Gly Val Pro Gly Val Gly Val Pro Gly Val Gly Val Pro Gly Gly Gly
                485                 490                 495
Val Pro Gly Ala Gly Val Pro Gly Val Gly Val Pro Gly Val Gly Val
                500                 505                 510
Pro Gly Val Gly Val Pro Gly Gly Gly Val Pro Gly Ala Gly Val Pro
        515                 520                 525
Gly Gly Gly Val Pro Gly Val Gly Val Pro Gly Val Gly Val Pro Gly
        530                 535                 540
Gly Gly Val Pro Gly Ala Gly Val Pro Gly Val Gly Val Pro Gly Val
545                 550                 555                 560
Gly Val Pro Gly Val Gly Val Pro Gly Gly Gly Val Pro Gly Ala Gly
                565                 570                 575
Val Pro Gly Gly Gly Val Pro Gly Val Gly Val Pro Gly Val Gly Val
                580                 585                 590
Pro Gly Gly Gly Val Pro Gly Ala Gly Val Pro Gly Val Gly Val Pro
        595                 600                 605
Gly Val Gly Val Pro Gly Val Gly Val Pro Gly Gly Gly Val Pro Gly
        610                 615                 620
Ala Gly Val Pro Gly Gly Gly Val Pro Gly Trp Pro
625                 630                 635
```

METHOD FOR ADMINISTERING A SUSTAINED RELEASE FORMULATION

PRIORITY

This application is a continuation of U.S. application Ser. No. 14/646,273 filed May 20, 2015, which is a National Stage Entry of PCT/US13/71038 filed Nov. 20, 2013, which claims priority to U.S. Provisional Application No. 61/728,318, filed Nov. 20, 2012, the contents of each of which are hereby incorporated by reference in their entireties.

FIELD OF INVENTION

The present invention relates to pharmaceutical formulations for sustained release when administered at cold temperatures, and methods for delivering a treatment regimen with the sustained release formulations.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: PHAS-028/02US_SeqList_St25.txt, date recorded Nov. 20, 2016).

BACKGROUND

The effectiveness of peptide and small molecule drugs is often limited by the half-life of such drugs in the circulation, as well as difficulties in obtaining substantially constant plasma levels. For example, the incretin GLP-1 must be administered at relatively high doses to counter its short half-life in the circulation, and these high doses are associated with nausea, among other things. Murphy and Bloom, *Nonpeptidic glucagon-like peptide 1 receptor agonists: A magic bullet for diabetes? PNAS* 104 (3):689-690 (2007). Further, the peptide agent vasoactive intestinal peptide (VIP) exhibits a half-life, in some estimates, of less than one minute, making this agent impractical for pharmaceutical use. Domschke et al., *Vasoactive intestinal peptide in man: pharmacokinetics, metabolic and circulatory effects. Gut* 19:1049-1053 (1978); Henning and Sawmiller, *Vasoactive intestinal peptide: cardiovascular effects, Cardiovascular Research* 49:27-37 (2001). A short plasma half life for peptide drugs is often due to fast renal clearance as well as to enzymatic degradation during systemic circulation.

Strategies for improving the pharmacokinetics of peptide and small molecule drugs are in great demand.

SUMMARY OF THE INVENTION

The present invention provides pharmaceutical formulations for sustained release, and methods for delivering a treatment regimen with the sustained release formulations. The invention thereby provides improved pharmacokinetics for peptide and small molecule drugs.

In one aspect, the invention provides a sustained release pharmaceutical formulation. The formulation comprises a therapeutic agent for systemic administration, where the therapeutic agent comprises an active agent and an amino acid sequence capable of forming a reversible matrix at the body temperature of a subject. The reversible matrix is formed from hydrogen bonds (e.g., intra- and/or intermolecular hydrogen bonds) as well as from hydrophobic contributions. The formulation further comprises one or more pharmaceutically acceptable excipients and/or diluents inducing the formation of the matrix upon administration. The matrix provides for a slow absorption to the circulation from an injection site. The sustained release, or slow absorption from the injection site, is due to a slow reversal of the matrix as the concentration dissipates at the injection site. Once product moves into the circulation, the formulation confers long half-life and improved stability. Thus, a unique combination of slow absorption and long half-life is achieved leading to a desirable PK profile with a shallow peak to trough ratio and/or long Tmax. In accordance with the invention, these benefits can be provided by administering cold formulations (e.g. 2-15° C., or 2-1.0° C., or 2-5° C.) of the therapeutic agent.

In certain embodiments, the amino acid sequence is an Elastin-Like-Protein (ELP) sequence. The ELP sequence comprises or consists of structural peptide units or sequences that are related to, or mimics of, the elastin protein. The amino acid sequence may exhibit a visible and reversible inverse phase transition with the selected formulation. That is, the amino acid sequence may be structurally disordered and highly soluble in the formulation below a transition temperature (Tt), but exhibit a sharp (2-3° C. range) disorder-to-order phase transition when the temperature of the formulation is raised above the Tt. In addition to temperature, length of the amino acid polymer, amino acid composition, ionic strength, pH, pressure, selected solvents, presence of organic solutes, temperature, and protein concentration may also affect the transition properties, and these may be tailored for the desired absorption profile. Other exemplary sequences or structures for the amino acid sequence forming the matrix are disclosed herein.

In various embodiments, the active agent for systemic administration is a protein or peptide, which may have a short circulatory half-fife, such as from about 30 seconds to about 1 hour, to about 2 hours, or to about 5 hours. In some embodiments, the protein or peptide has a circulatory half-life of from 30 seconds to about 10 hours. The therapeutic agent may be a recombinant fusion protein between the protein active agent and the amino acid sequence capable of forming the matrix. Exemplary peptide active agents include GLP-1 receptor agonists (e.g., GLP-1 or derivative thereof), glucagon receptor agonists (e.g. glucagon, oxyntomodulin or derivatives thereof), VPAC2 selective agonists (e.g. vasoactive intestinal peptide (VIP) or a derivative thereof), (GIP receptor agonists (e.g. glucose-dependent insulinotropic peptide (GIP) or a derivative thereof) or insulin or a derivative thereof. Alternatively, the protein active agent is a clotting factor, such as Factor VII, Factor VIII, or Factor IX. Other protein and small molecule drugs for delivery in accordance with the invention are disclosed herein. By providing a slow absorption from the injection site, renal clearance and degradation can be controlled thereby achieving the desired PK profile.

In another aspect, the invention provides a method for delivering a sustained release regimen of an active agent. The method comprises administering the formulation described herein to a subject in need, wherein the formulation is administered from about 1 to about 8 times per month. In some embodiments, the formulation is administered about weekly, and may be administered subcutaneously or intramuscularly (for example). In some embodiments, the site of administration is not a pathological site, that is, the therapeutic agent is not administered directly to the intended site of action.

DESCRIPTION OF THE DRAWINGS

FIG. 1 shows the phase transition (as shown by an increase in turbidity) of an ELP1 protein, induced by a change in temperature to 37° C. or above. This property provides for a slow absorption from an injection site.

FIG. 6 shows a summary of pharmacokinetic parameters for Glp-1/ELP1-120 (also referred to herein as PB1023 or Glymera) after SC administration of 0.3, 0.6, 0.9 and 1.35 mg/kg to adult subjects with type 2 diabetes mellitus.

FIG. 9 shows a summary of pharmacokinetic parameters for Glymera after s.c. administration of 90 mg as 50 mg/mL and 100 mg/mL formulations to adult subjects with type 2 diabetes mellitus.

FIG. 10 shows a summary of pharmacokinetic parameters for PB1023 after SC administration of 90 mg as 50 mg/mL and 100 mg/mL formulations at room temperature and 100 mg/mL cold (2° to 8° C.) to adult subjects with T2DM.

FIG. 11 shows a statistical comparison of pharmacokinetic parameters for PB1023 alter SC administration of 90 mg as 50 mg/mL and 100 mg/mL formulations at room temperature and 100 mg/mL, cold (2° to 8° C.) to adult subjects with T2DM.

FIG. 14 shows a summary of pharmacokinetic parameters for PB1023 after SC administration of 90 mg as 50 mg/mL, and 100 mg/mL, formulations to adult subjects with T2DM.

FIG. 15 shows a statistical comparison of pharmacokinetic parameters for PB1023 after SC administration of 90 mg as 50 mg/mL and 100 mg/mL formulations to adult subjects with T2DM.

FIG. 18 shows a summary of pharmacokinetic parameters for PB1023 after SC administration of 90 mg as the 100 mg/mL formulation at room temperature and 100 mg/mL cold (2° to 8° C.) to adult subjects with T2DM.

FIG. 19 shows a statistical comparison of pharmacokinetic parameters for PB1023 after SC administration of 90 mg as the 100 mg/mL formulation at room temperature and 100 mg/mL cold (2° to 8° C.) to adult subjects with T2DM.

FIG. 20A shows the human proinsulin sequence (SEQ ID NO: 23). The proinsulin sequence consists of the B and A chains linked with the C peptide. The C peptide is removed to form mature insulin following enzymatic cleavage at the two adjacent dibasic sites (underlined in italics).

FIG. 20B shows the amino acid sequence of a proinsulin ELP1-120 fusion protein (SEQ ID NO: 24). The proinsulin sequence (underlined) is fused to the ELP1-120 sequence. The amino acid sequence optionally includes an initiation methionine residue at the N terminus.

FIG. 21 shows the amino acid sequence of a GLP-1/ELP fusion protein (SEQ ID NO: 25) as described herein.

DETAILED DESCRIPTION

Figure 2:
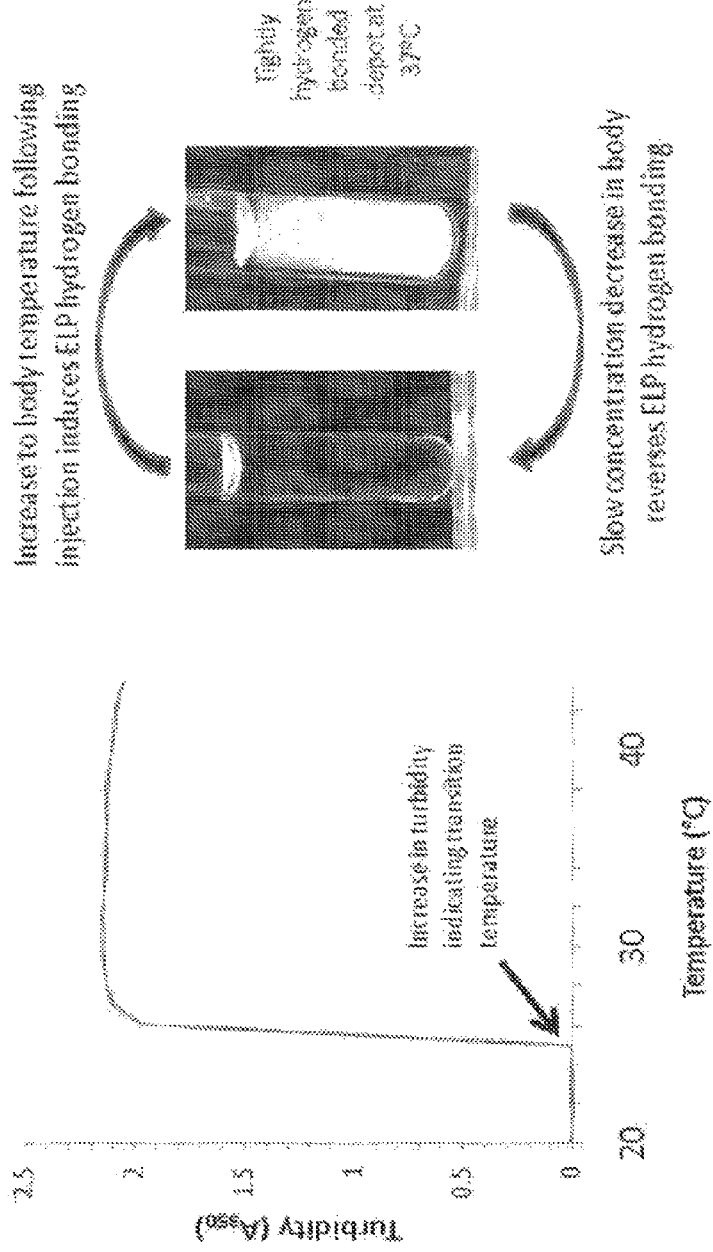
FIG. 2 shows the phase transition (as shown by an increase in turbidity) of an ELP4 protein, induced by a change in temperature to 25° C. or above. This property provides for a depot-like delivery.

The present invention provides pharmaceutical formulations for sustained release, and methods for delivering a treatment regimen with the sustained release formulations. The invention thereby provides improved pharmacokinetics for peptide and small molecule drugs, including a relatively flat PK profile with a low ratio of peak to trough, and/or a long Tmax. The PK profile can be maintained with a relatively infrequent administration schedule, such as from one to eight injections per month in some embodiments.

In one aspect, the invention provides a sustained release pharmaceutical formulation. The formulation comprises a therapeutic agent for systemic administration, where the therapeutic agent comprises an active agent and an amino acid sequence capable of forming a matrix at the body temperature of a subject. The reversible matrix is formed from hydrogen bonds (e.g., intra- and/or intermolecular hydrogen bonds) as well as from hydrophobic contributions. The formulation further comprises one or more pharmaceutically acceptable excipients and/or diluents inducing the formation of the matrix upon administration. The matrix provides for a slow absorption to the circulation from an injection site, and without being bound by theory, this slow absorption is due to the slow reversal of the matrix as protein concentration decreases at the injection site. The slow absorption profile provides for a flat PK profile, as well as convenient and comfortable administration regimen. For example, in various embodiments, the plasma concentration of the active agent over the course of days (e.g., from 2 to about 60 days, or from about 4 to about 30 days) does not change by more than a factor of 10, or by more than a factor of about 5, or by more than a factor of about 3. Generally, this flat PK profile is seen over a plurality of (substantially evenly spaced) administrations, such as at least 2, at least about 5, or at least about 10 administrations of the formulation. In some embodiments, the slow absorption is exhibited by a Tmax (time to maximum plasma concentration) of greater than about 5 hours, greater than about 10 hours, greater than about 20 hours, greater than about 30 hours, or greater than about 50 hours.

The sustained release, or slow absorption from the injection site, is controlled by the amino acid sequence capable of forming a hydrogen-bonded matrix at the body temperature of the subject, as well as the components of the formulation.

In some embodiments, the amino acid sequence contains structural units that farm hydrogen-bonds through protein backbone groups and/or side chain groups, and which may contribute hydrophobic interactions to matrix formation. In some embodiments, the amino acids side chains do not contain hydrogen bond donor groups, with hydrogen bonds being formed substantially through the protein backbone. Exemplary amino acids include proline, alanine, valine, glycine, and isoleucine, and similar amino acids. In some embodiments, the structural units are substantially repeating structural units, so as to create a substantially repeating structural motif, and substantially repeating hydrogen-bonding capability. In these and other embodiments, the amino acid sequence contains at least 10%, at least 20%, at least 40%, or at least 50% proline, which may be positioned in a substantially repeating pattern. In this context, a substantially repeating pattern means that at least 50% or at least 75% of the proline residues of the amino acid sequence are part of a definable structural unit. In still other embodiments, the amino acid sequence contains amino acids with hydrogen-bond donor side chains, such as serine, threonine, and/or tyrosine. In some embodiments, the repeating sequence may contain from one to about four proline residues, with remaining residues independently selected from non-polar residues, such as glycine, alanine, leucine, isoleucine, and valine. Non-polar or hydrophobic residues may contribute hydrophobic interactions to the formation of the matrix.

The amino acid sequences may form a "gel-like" state upon injection at a temperature higher than the storage temperature. Exemplary sequences have repeating peptide units, and/or may be relatively unstructured at the lower temperature, and achieve a hydrogen-bonded, structured, state at the higher temperature.

In some embodiments, the amino acid sequence capable of forming the matrix at body temperature is a peptide hiving repeating units of from four to ten amino acids. The repeating unit may form one, two, or three hydrogen bonds in the formation of the matrix. In certain embodiments, the amino acid sequence capable of forming the matrix at body temperature is an amino acid sequence of silk, elastin, collagen, or keratin, or mimic thereof, or an amino acid sequence disclosed in U.S. Pat. No. 6,355,776, which is hereby incorporated by reference.

In certain embodiments, the amino acid sequence is an Elastin-Like-Protein (ELP) sequence. The ELP sequence comprises or consists of structural peptide units or sequences that are related to, or mimics of, the elastin protein. The ELP sequence is constructed from structural units of from three to about twenty amino acids, or in some embodiments, from four to ten amino acids, such as four, five or six amino acids. The length of the individual structural units may vary or may be uniform. Exemplary structural units include units defined by SEQ ID NOS: 1-12 (below), which may be employed as repeating structural units, including tandem-repeating units, or may be employed in some combination. Thus, the ELP may comprise or consist essentially of structural unit(s) selected from SEQ ID NOS: 1-12, as defined below.

In some embodiments, including embodiments in which the structural units are ELP units, the amino acid sequence comprises or consists essentially of from about 10 to about 500 structural units, or in certain embodiments about 50 to about 200 structural units, or in certain embodiments from about 80 to about 200 structural units, or from about 80 to about 150 structural units, such as one or a combination of units defined by SEQ ID NOS: 1-12. Thus, the structural units collectively may have a length of from about 50 to about 2000 amino acid residues, or from about 100 to about 800 amino acid residues, or from about 200 to about 700 amino acid residues, or from about 400 to about 600 amino acid residues.

The amino acid sequence may exhibit a visible and reversible inverse phase transition with the selected formulation. That is, the amino acid sequence may be structurally disordered and highly soluble in the formulation below a transition temperature (Tt), but exhibit a sharp (2-3° C. range) disorder-to-order phase transition when the temperature of the formulation is raised above the Tt. In addition to temperature, length of the amino acid polymer, amino acid composition, ionic strength, pH, pressure, temperature, selected solvents, presence of organic solutes, and protein concentration may also affect the transition properties, and these may be tailored in the formulation for the desired absorption profile. Absorption profile can be easily tested by determining plasma concentration or activity of the active agent over time.

In certain embodiments, the ELP component(s) may be formed of structural units, including but not limited to:
  (a) the tetrapeptide Val-Pro-Gly-Gly, or VPGG (SEQ ID NO: 1);
  (b) the tetrapeptide Ile-Pro-Gly-Gly, or IPGG (SEQ ID NO: 2);
  (c) the pentapeptide Val-Pro-Gly-X-Gly (SEQ ID NO: 3), or VPGXG, where X is any natural or non-natural amino acid residue, and where X optionally varies among polymeric or oligomeric repeats;
  (d) the pentapeptide Ala-Val-Gly-Val-Pro, or AVGVP (SEQ ID NO: 4);
  (e) the pentapeptide Ile-Pro-Gly-X-Gly, or IPDXO (SEQ ID NO: 5), where X is any natural or non-natural amino acid residue, and where X optionally varies among polymeric or oligomeric repeats;
  (e) the pentapeptide Ile-Pro-Gly-Val-Gly, or IPGVG (SEQ ID NO: 6);
  (f) the pentapeptide Leu-Pro-Gly-X-Gly, or LPGXG (SEQ ID NO: 7), where X is any natural or non-natural amino acid residue, and where X optionally varies among polymeric or oligomeric repeats;
  (g) the pentapeptide Leu-Pro-Gly-Val-Gly, or LPGVG (SEQ ID NO: 8);
  (h) the hexapeptide Val-Ala-Pro-Gly-Val-Gly, or VAPGVG (SEQ ID NO: 9):
  (i) the octapeptide Gly-Val-Gly-Val-Pro-Gly-Val-Gly, or GVGVPGVG (SEQ ID NO: 10);
  (j) the nonapeptide Val-Pro-Gly-Phe-Gly-Val-Gly-Ala-Gly, or VPGFGVGAG (SEQ ID NO: 11); and
  (k) the nonapeptides Val-Pro-Gly-Val-Gly-Val-Pro-Gly-Gly, or VPGVGVPGG (SEQ ID NO: 12).

Such structural units defined by SEQ ID NOS:1-12 may firm structural repeat units, or may be used in combination to form an ELP. In some embodiments, the ELP component is formed entirely (or almost entirely) of one or a combination of (e.g., 2, 3 or 4) structural units selected from SEQ ID NOS: 1-12. In other embodiments, at least 75%, or at least 80%, or at least 90% of the ELP component is formed from one or a combination of structural units selected from SEQ ID NOS: 1-12, and which may be present as repeating units.

In certain embodiments, the ELP contains repeat units, including tandem repeating units, of Val-Pro-Gly-X-Gly (SEQ ID NO: 3), where X is as defined above, and where the percentage of Val-Pro-Gly-X-Gly (SEQ ID NO: 3) units taken with respect to the entire ELP component (which may comprise structural units other than VPGXG (SEQ ID NO: 3)) is greater than about 50%, or greater than about 75%, or greater than about 85%, or greater than about 95% of the ELP. The ELP may contain motifs of 5 to 15 structural units (e.g. about 10 structural units) of SEQ ID NO: 3, with the guest residue X varying among at least 2 or at least 3 of the units in the motif. The guest residues may be independently selected, such as from non-polar or hydrophobic residues, such as the amino acids V, I, L, A, G, and W (and may be selected so as to retain a desired inverse phase transition property).

In some embodiments, the ELP may form a β-turn structure. Exemplary peptide sequences suitable tier creating a β-turn structure are described in International Patent Application PCT/US96/05186, which is hereby incorporated by reference in its entirety. For example, the fourth residue (X) in the sequence VPGXG (SEQ ID NO: 3), can be altered without eliminating the formation of a β-turn.

The structure of exemplary ELPs may be described using the notation ELPk [XiYj-n], where k designates a particular ELP repeat unit, the bracketed capital letters are single letter amino acid codes and their corresponding subscripts designate the relative ratio of each guest residue X in the structural units (where applicable), and n describes the total length of the [[P in number of the structural repeats. For example, ELP1 [V5A2G3-10] designates an ELP component containing 10 repeating units of the pentapeptide VPGXG (SEQ ID NO: 3), where X is valine, alanine, and glycine at a relative ratio of about 5:2:3; ELP1 [K1V2F1-4] designates an ELP component containing 4 repeating units of the pentapeptide VPGXG (SEQ ID NO: 3), where X is lysine, valine, and phenylalanine at a relative ratio of about 1:2:1; ELP1 [K1V7F1-9] designates a polypeptide containing 9 repeating units of the pentapeptide VPGXG (SEQ ID NO: 3), where X is lysine, valine, and phenylalanine at a relative ratio of about 1:7:1; ELP1 [V-5] designates a polypeptide containing 5 repeating units of the pentapeptide VPGXG (SEQ ID NO: 3), where X is valine; ELP1 [V-20] designates a polypeptide containing 20 repeating units of the pentapeptide VPGXG (SEQ ID NO: 3), where X is valine; ELP2 [5] designates a polypeptide containing 5 repeating units of the pentapeptide AVGVP (SEQ ID NO: 4); ELP3 [V-5] designates a polypeptide containing 5 repeating units of the pentapeptide IPGXG (SEQ ID NO: 5), where X is valine; ELP4 [V-5] designates a polypeptide containing 5 repeating units of the pentapeptide LPGXG (SEQ ID NO: 7), where X is valine.

With respect to ELP, the Tt is a function of the hydrophobicity of the guest residue. Thus, by varying the identity of the guest residue(s) and their mole fraction(s), ELPs can be synthesized that exhibit an inverse transition over a broad range. Thus, the Tt at a given ELP length may be decreased by incorporating a larger fraction of hydrophobic guest residues in the ELP sequence. Examples of suitable hydrophobic guest residues include valine, leucine, isoleucine, phenylalanine, tryptophan and methionine. Tyrosine, which is moderately hydrophobic, may also be used. Conversely, the It may be increased by incorporating residues, such as those selected from: glutamic acid, cysteine, lysine, aspartate, alanine, asparagine, serine, threonine, glycine, arginine, and glutamine.

For polypeptides having a molecular weight>100,000, the hydrophobicity scale disclosed in PCT/US96/05186 (which is hereby incorporated by reference in its entirety) provides one means far predicting the approximate Tt of a specific ELP sequence. For polypeptides having a molecular weight<100,000, the Tt may be predicted or determined by the following quadratic function: $Tt=M0+M1X+M2X2$ where X is the MW of the fusion protein, and $M0=116.21$; $M1=-1.7499$; $M2=0.010349$.

The ELP in some embodiments is selected or designed to provide a Tt ranging from about 10 to about 37° C. at formulation conditions, such as from about 20 to about 37° C., or from about 25 to about 37° C. In some embodiments, the transition temperature at physiological conditions (e.g., 0.9% saline) is from about 34 to 36° C., to take into account a slightly lower peripheral temperature.

In certain embodiments, the amino acid sequence capable of farming the hydrogen-bonded matrix at body temperature comprises $[VPGXG]_{90}$, where each X is selected from V, G, and A, and wherein the ratio of V:G:A may be about 5:3:2. For example, the amino acid sequence capable of forming the hydrogen-bonded matrix at body temperature may comprise $[VPGXG]_{120}$, where each X is selected from V, G, and A, and wherein the ratio of V:G:A may be about 5:3:2. As shown herein, 120 structural units of this ELP can provide a transition temperature at about 37° C. with about 5 to 15 mg/ml. (e.g., about 10 mg/ml) of protein. At concentrations of about 50 to about 100 mg/mL the phase transition temperature is about 35.5 degrees centigrade (just below body temperature), which allows for peripheral body temperature to be just less than 37° C.

Alternatively, the amino acid sequence capable of forming the matrix at body temperature comprises $[VPGVG]_{90}$, or $[VPGVG]_{120}$. As shown herein, 120 structural units of this ELP can provide a transition temperature at about 37° C. with about 0.005 to about 0.05 mg/ml (e.g., about 0.01 mg/ml) of protein.

Elastin-like-peptide (ELP) protein polymers and recombinant fusion proteins can be prepared as described in U.S. Patent Publication No. 2010/0022455, which is hereby incorporated by reference.

In other embodiments, the amino acid sequence capable of forming the matrix at body temperature may include a random coil or non-globular extended structure. For example, the amino acid sequence capable of forming the matrix at body temperature may comprise an amino acid sequence disclosed in U.S. Patent Publication No. 2008/0286808, WIPO Patent Publication No. 2008/155134, and U.S. Patent Publication No. 2011/0123487, each of which is hereby incorporated by reference.

For example, in some embodiments the amino acid sequence comprises an unstructured recombinant polymer of at least 40 amino acids. For example, the unstructured polymer may be defined where the sum of glycine (G), aspartate (D), alanine (A), serine (S), threonine (T), glutamate (E) and proline (P) residues contained in the unstructured polymer, constitutes more than about 80% of the total amino acids. In some embodiments, at least 50% of the amino acids are devoid of secondary structure as determined by the Chou-Fasman algorithm. The unstructured polymer may comprise more than about 100, 150, 200 or more contiguous amino acids. In some embodiments, the amino acid sequence forms a random coil domain. In particular, a polypeptide or amino acid polymer having or forming "random coil conformation" substantially lacks a defined secondary and tertiary structure.

In various embodiments, the intended subject is human, and the body temperature is about 37° C., and thus the therapeutic agent is designed to provide a sustained release at this temperature. A slow release into the circulation with reversal of hydrogen bonding and/or hydrophobic interactions is driven by a drop in concentration as the product diffuses at the injection site, even though body temperature remains constant. In other embodiments, the subject is a non-human mammal, and the therapeutic agent is designed to exhibit a sustained release at the body temperature of the mammal, which may be from about 30 to about 40° C. in some embodiments, such as for certain domesticated pets (e.g., dog or cat) or livestock (e.g., cow, horse, sheep, or pig). Generally, the Tt is higher than the storage conditions of the formulation. The storage conditions may be from about 2 to about 22° C., including about 2 to about 3° C., about 2 to about 4° C., about 2 to about 5° C., about 2 to about 6° C., about 2 to about 7° C., about 2 to about 8° C., about 2 to about 10° C., about 2 to about 12° C., about 2 to about 14° C., about 2 to about 16° C., about 10 to about 25° C., or from 15 to 22° C., such that the therapeutic agent remains in solution for injection and exhibits the desired pharmacokinetic behavior. The formulation may be administered at the about storage temperature.

The therapeutic agent is generally for "systemic delivery," meaning that the agent is not delivered locally to a pathological site or a site of action. Instead, the agent is absorbed into the bloodstream from the injection site, where the agent acts systemically or is transported to a site of action via the circulation.

In various embodiments, the active agent is a protein or peptide, which may have a short circulatory half-life, such as from about 30 seconds to about 1 hour. The therapeutic agent may be a recombinant fusion protein between the protein active agent and the amino acid sequence capable of forming the hydrogen-bonded matrix at the body temperature of the subject. Exemplary peptide active agents include GIP receptor agonists such as glucose-dependent insulinotropic peptide (GIP) or a derivative thereof. Further exemplary peptide active agents include GLP1 receptor agonists such as GLP-1 or derivative thereof (including GLP1 7-36 or GLP1 7-37), or exendin-4 or derivative thereof. GLP1 7-36 has the following amino acid sequence: HAEGTFTSDVS-SYLEGQAAKEFIAWLVKGR (SEQ ID NO: 17). Exendin-4 has the following amino acid sequence: HGEGTFTS-DLSKQMEEEAVRLFIEWLKNGGPSSGAPPPS (SEQ ID NO: 18). In other embodiments, the protein or peptide agent is a glucagon receptor agonist (including glucagon, oxyntomodulin or a derivative thereof). Oxyntomodulin, has the amino acid sequence HSQGTFTSDYSKYLDSRRAQD-FVQWLMNTKRNKNNIA (SEQ ID NO: 19). Glucagon has the amino acid sequence HSQGTFTSDYSKYLDSR-RAQDFVQWLMNT (SEQ ID NO: 20). GLP-2 has the amino acid sequence HADGSFSDEMNTILDNLAARD-FINWLIQTKITD (SEQ ID NO: 21). The amino acid sequence of GIP is YAEGTFISDYSIAMDKIRQQDFVN-WLLAQ (SEQ ID NO: 22). In some embodiments, the GLP-1 receptor agonist is a dual agonist having an amino acid sequence described in US 2011/0257092, which is hereby incorporated by reference in its entirety. Other dual or multi receptor agonists are described in US 2011/016602 and US 2010/00190701, each of which is hereby incorporated by reference, in particular with regard to the structures and sequences of GLP-1 receptor co-agonists described therein. Additional descriptions of GLP-1 receptor co-agonists can be found in Pocai A et al., Glucagon-Like Peptide 1/Glucagon Receptor Dual Agonism Reverses Obesity in Mice, *Diabetes* 58:2258-2266 (2009) and Patterson J T et al., Functional association of the N-terminal residues with the central region in glucagon-related peptides, *J. Pept. Sci.* 17:659-666 (2011), each of which are hereby incorporated by reference in their entirety. In another embodiment, the invention provides for a co-formulation of any two of a GLP1 receptor agonist, a glucagon receptor agonist, and a GIP receptor agonist. In other embodiments, the protein or peptide agent is a VPAC2 selective agonist, such as vasoactive intestinal peptide (VIP) or a derivative thereof. Alternatively, the protein active agent is a clotting factor, such as Factor VII, Factor VIII, or Factor IX, or in other embodiments is insulin (e.g., single chain insulin or an A chain or a B chain fusion protein, as described in U.S. Provisional Application No. 61/563,985, which is hereby incorporated by reference) or a monoclonal antibody or single chain antibody. Alternatively, the active agent is as described in U.S. Patent Publication No. 2011/0123487, which is hereby incorporated by reference. Exemplary therapeutic agents in accordance with the invention include GLP-1 (A8G,7-37) ELP1-120 (referred to herein as PB1023) or GLP-1 (A8G, 7-37) ELP4-120 (PB1046). By providing a slow absorption from the injection site, renal clearance and degradation can be controlled, thereby achieving the desired PK profile.

In various embodiments, the invention encompasses formulations which comprise a therapeutic agent for systemic administration, where the therapeutic agent comprises an active agent selected from one or more of insulin (by way of non-limiting example, single chain insulin or an A chain or a B chain fusion protein) and GLP-1 or derivative thereof (by way of non-limiting example, GLP1 7-36 or GLP1 7-37) and an amino acid sequence capable of forming a matrix at the body temperature of a subject (by way of non-limiting example, ELP). In various embodiments, the present invention encompasses a formulation, or co-formulation, of GLP-1 or derivative thereof (including GLP1 7-36 or GLP1 7-37) fused to ELP and insulin (by way of non-limiting example, single chain insulin or an A chain or a B chain fusion protein) fused to ELP. In some embodiments, these formulations are administered cold (by way of non-limiting example, 2-10° C.) or at room temperature as described herein.

In various embodiments, the invention encompasses doses and/or regimens such as those that do not induce substantial appetite suppression in a patient and/or those that do not induce substantial nausea in the patient, such as those described in PCT/US12/44383, which is hereby incorporated by reference.

In other embodiments, the therapeutic agent is a chemical conjugate between the active agent and the amino acid sequence capable of forming the matrix at the body temperature of the subject. For example, the active agent may be a chemotherapeutic agent, such as a chemotherapeutic agent selected from methotrexate, daunomycin, mitomycin, cisplatin, vincristine, epirubicin, fluorouracil, verapamil, cyclophosphamide, cytosine arabinoside, aminopterin, bleomycin, mitomycin C, democolcine, etoposide, mithramycin, chlorambucil, melphalan, daunoubicin, doxorubicin, tamoxifen, paclitaxel, vinblastine, camptothecin, actinomycin 13, cytarabine, and combrestatin. Alternatively, the agent may be an immunogenic molecule, or an immunomodulator, or an anti-inflammatory agent, such as an agent described in U.S. Patent Publication No. 2009/0004104, which is hereby incorporated by reference in its entirety. Also, the agent may be an opioid molecule, such as, for example oxycodone, morphine, or codeine such as described in U.S. Provisional Application No. 61/597,898, which is hereby incorporated by reference. The chemical conjugate may be through a cleavable linker, for which numerous types are known in the art. See U.S. Pat. No. 6,326,996, which is hereby incorporated by reference in its entirety.

The formulation comprises one or more pharmaceutically acceptable excipients and/or diluents inducing the formation of the matrix upon administration. For example, such excipients include salts, and other excipients that may act to stabilize hydrogen bonding. Exemplary salts include alkaline earth metal salts such as sodium, potassium, and calcium. Counter ions include chloride and phosphate. Exemplary salts include sodium chloride, potassium chloride, magnesium chloride, calcium chloride, and potassium phosphate.

The protein concentration in the formulation is tailored to drive, along with the excipients, the formation of the matrix at the temperature of administration. For example, higher protein concentrations help drive the formation of the matrix, and the protein concentration needed for this purpose varies depending on the ELP series used. For example, in embodiments using an ELP1-120, or amino acid sequences with comparable transition temperatures, the protein is present in the range of about 1 mg/mL, to about 200 mg/mL, or is present in the range of about 5 mg/mL, to about 125 mg/mL. The therapeutic agent may be present in the range of about 10 mg/mL to about 50 mg/mL, or about 15 mg/mL to about 30 mg/mL. In embodiments using an ELP4-120, or amino acid sequences with comparable transition temperatures, the protein is present in the range of about 0.005 mg/mL to about 10 mg/mL, or is present in the range of about 0.01 mg/mL to about 5 mg/mL.

The therapeutic agent is formulated at a pH, ionic strength, and generally with excipients sufficient to drive the formation of the matrix at body temperature (e.g., 37° C., or at from 34 to 36° C. in some embodiments). The therapeutic agent is generally prepared such that it does not form the matrix at storage conditions. Storage conditions are generally less than the transition temperature of the formulation, such as less than about 32° C., or less than about 30° C., or less than about 27° C., or less than about 25° C., or less than about 20° C., or less than about 15° C. For example, the formulation may be isotonic with blood or have an ionic strength that mimics physiological conditions. For example, the formulation may have an ionic strength of at least that of 25 mM Sodium Chloride, or at least that of 30 mM Sodium chloride, or at least that of 40 mM Sodium Chloride, or at least that of 50 mM Sodium Chloride, or at least that of 75 mM Sodium Chloride, or at least that of 100 mM Sodium Chloride, or at least that of 150 mM Sodium Chloride. In certain embodiments, the formulation has an ionic strength less than that of 0.9% saline. In some embodiments, the formulation comprises two or more of calcium chloride, magnesium chloride, potassium chloride, potassium phosphate monobasic, sodium chloride, and sodium phosphate dibasic. The liquid formulation may comprise the components listed in Table 4, Table 5, or Table 6, and can be stored refrigerated or at room temperature.

The formulation can be packaged in the form of pre-dosed pens or syringes for administration once per week, twice per week, or from one to eight times per month, or alternatively filled in conventional vial and the like.

In exemplary embodiments, the invention provides a sustained release pharmaceutical formulation that comprises a therapeutic agent, the therapeutic agent (e.g., a peptide or protein therapeutic agent) comprising an active agent and an amino acid sequence comprising $[VPGXG]_{90}$, or $[VPGXG]_{120}$, where each X is selected from V, G, and A. V, G, and A may be present at a ratio of about 5:3:2. Alternatively, the amino acid sequence comprises $[VPGXG]_{90}$, or $[VPGXG]_{120}$. The formulation further comprises one or more pharmaceutically acceptable excipients and/or diluents for formation of a reversible matrix from an aqueous form upon administration to a human subject. The active agent in certain embodiments is GLP-1 or derivative thereof (e.g., GLP-1, A8G, 7-37), or vasoactive intestinal peptide (VIP) or a derivative thereof (e.g., having an N-terminal moiety such as a Methionine), or oxyntomodulin of a derivative thereof, or insulin or a derivative thereof. GLP-1 and derivatives thereof are disclosed in U.S. Patent Publication No. 2011/0123487, which is hereby incorporated by reference. VIP and derivatives thereof are disclosed in U.S. Patent Publication No. 2011/0178017, which is hereby incorporated by reference. Insulin and derivatives thereof are described in U.S. Provisional Application No. 61/563,985, which is hereby incorporated by reference.

In these embodiments, the therapeutic agent may be present in the range of about 0.5 mg/mL to about 200 mg/mL, or is present in the range of about 5 mg/mL to about 125 mg/ML. The therapeutic agent is present in the range of about 10 mg/mL to about 50 mg/nit, or the range of about 15 mg/mL, to about 30 mg/mL. The formulation may have an ionic strength of at least that of 25 mM Sodium Chloride, or at least that of 30 mg/mL sodium Chloride, or at least that of 40 mM Sodium Chloride, or at that least that of 50 mM Sodium Chloride, or at least that of 75 mM Sodium Chloride, or at least that of 100 mM Sodium Chloride. The formulation may have an ionic strength less than that of about 0.9% saline. The formulation comprises two or more of calcium chloride, magnesium chloride, potassium chloride, potassium phosphate monobasic, sodium chloride, and sodium phosphate dibasic. The formulation may comprise the components listed in Table 4, Table 5, or Table 6.

Other formulation components for achieving the desired stability, for example, may also be employed. Such components include one or more amino acids or sugar alcohol (e.g., mannitol), preservatives, and buffering agents, and such ingredients are well known in the art.

In another aspect, the invention provides a method for delivering a sustained release regimen of an active agent. The method comprises administering the formulation described herein to a subject in need, wherein the formulation is administered from about 1 to about 8 times per month (e.g., about weekly). For example, the active agent may be GLP-1 or an analog thereof, and is administered in a method described in U.S. patent application Ser. No. 13/534,836, which is hereby incorporated by reference. For example, the therapeutic agent may be GLP-1 7-36 or 7-37, alternatively having Gly at position 8, fused to ELP1 (e.g., having from about 90 to about 150 ELP units). The GLP-1 fusion may be used for the treatment of diabetes (type 1 or 2), metabolic disease, or obesity, for example, by administering to a patient in need. Alternatively, the active agent is VIP or an analog thereof, and is administered in a method described in U.S. Patent Publication No. 2011/0178017, which is hereby incorporated by reference. The VIP may have an additional moiety such as Methionine at the N-terminus to alter the receptor binding profile, as also described in U.S. Patent Publication No. 2011/0178017, which description is hereby incorporated by reference. The VIP may be fused to ELP1 (having from about 90 to about 150 ELP units). The VIP active agent finds use in a method of treating a condition selected from uncontrolled or resistant hypertension, or pulmonary arterial hypertension (PAH), and chronic obstructive pulmonary disease (COPD), among others. In other embodiments, the active agent is insulin, which finds use in methods (using the ELP-based regimens described herein) of treating diabetes, including type 1 or type 2 diabetes.

In some embodiments, the formulation is administered about weekly, and may be administered subcutaneously or intramuscularly. In some embodiments, the site of administration is not a pathological site, for example, is not the intended site of action.

In various embodiments, the plasma concentration of the active agent does not change by more than a factor of 10, or a factor of about 5, or a factor of about 3 over the course of a plurality of administrations, such as at least 2, at least about 5, or at least about 10 administrations of the formulation. The administrations are substantially evenly spaced, such as, for example, about daily, or about once per week, or from one to about five times per month.

In certain embodiments, the subject is a human, but in other embodiments may be a non-human mammal, such as a domesticated pet (e.g., dog or cat), or livestock or farm animal (e.g., horse, cow, sheep, or pig).

EXAMPLES

Figure 3:
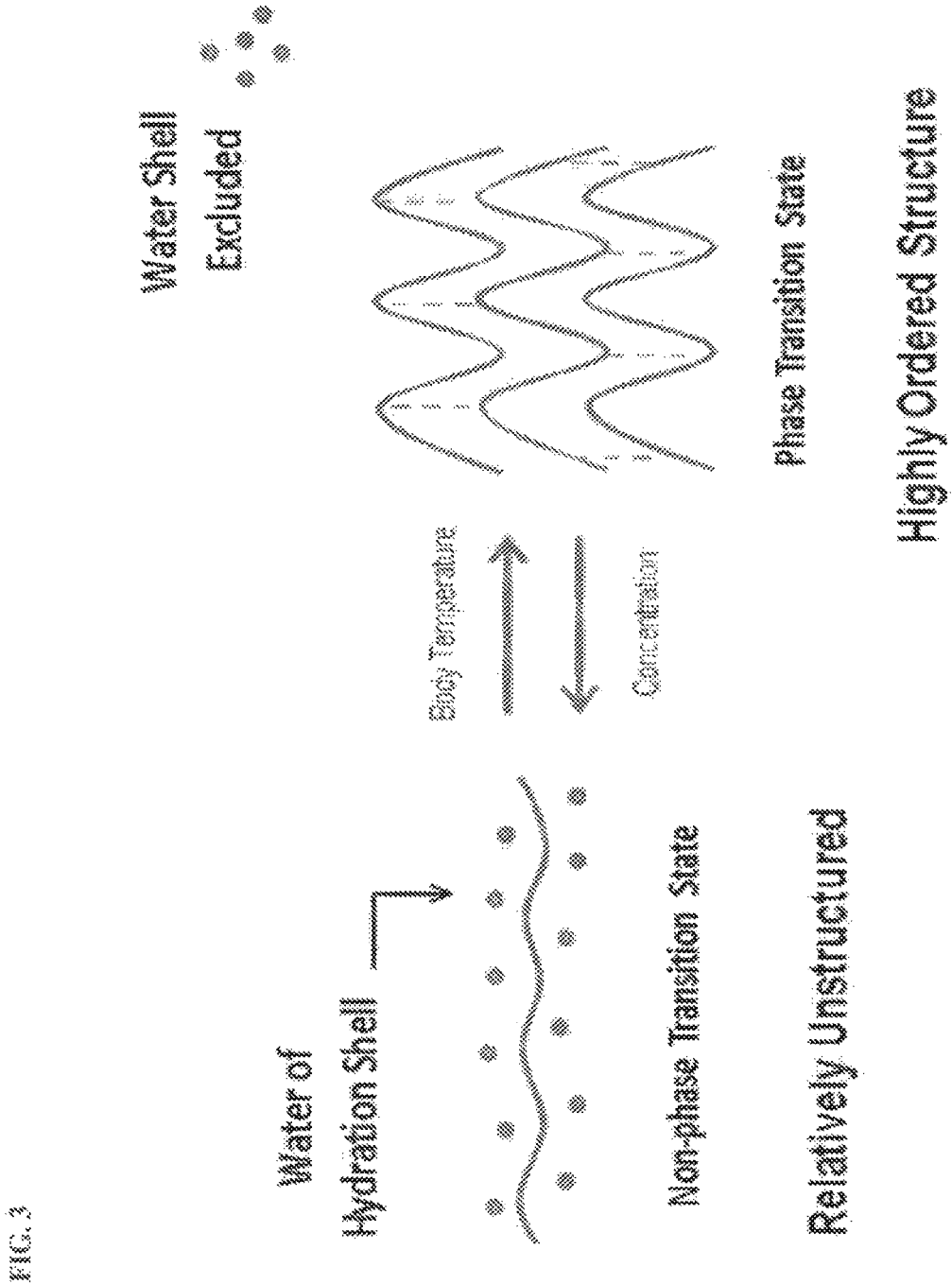
FIG. 3 illustrates, without wishing to be bound by theory, a potential mechanism for the observed transition, in which a water shell is excluded under certain conditions, allowing for hydrogen bonds to form.

The phase transition property exhibited by certain amino acid sequences is illustrated in FIG. 1 (for ELP1) and FIG. 2 (for ELP4). Phase transition can be observed as an increase in turbidity. FIG. 3 illustrates, without wishing to be bound by theory, a potential mechanism for phase transition, driven by exclusion of a water shell and formation of hydrogen bonds at a temperature above the phase transition temperature for a given concentration.

Figure 4:
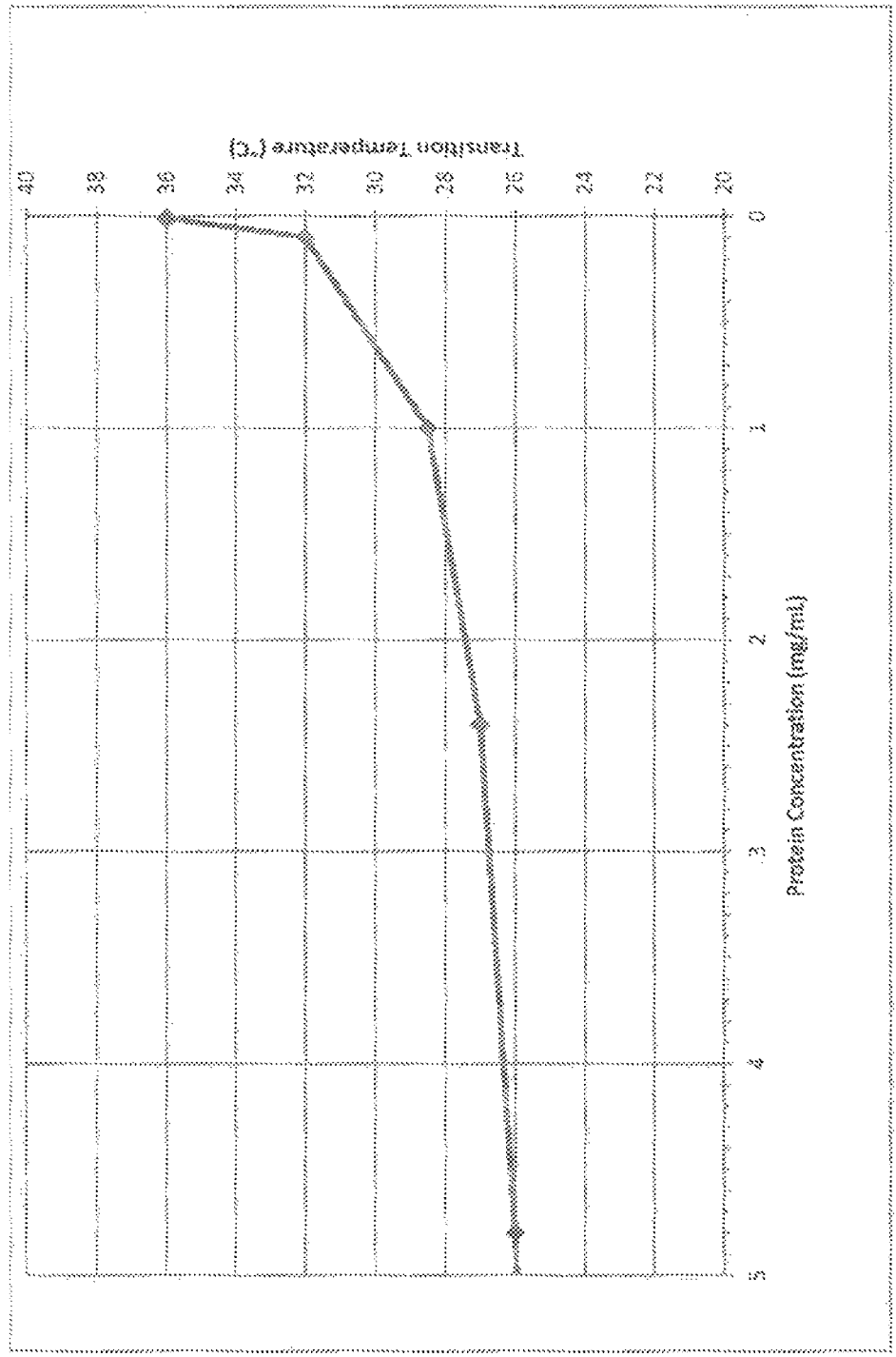
FIG. 4 shows that the ELP4 series transitions at 37° C. at a protein concentration of less than about 0.01 mg/ml, allowing for sustained release formulations of low protein concentration, for example, at the injection site
Figure 5:
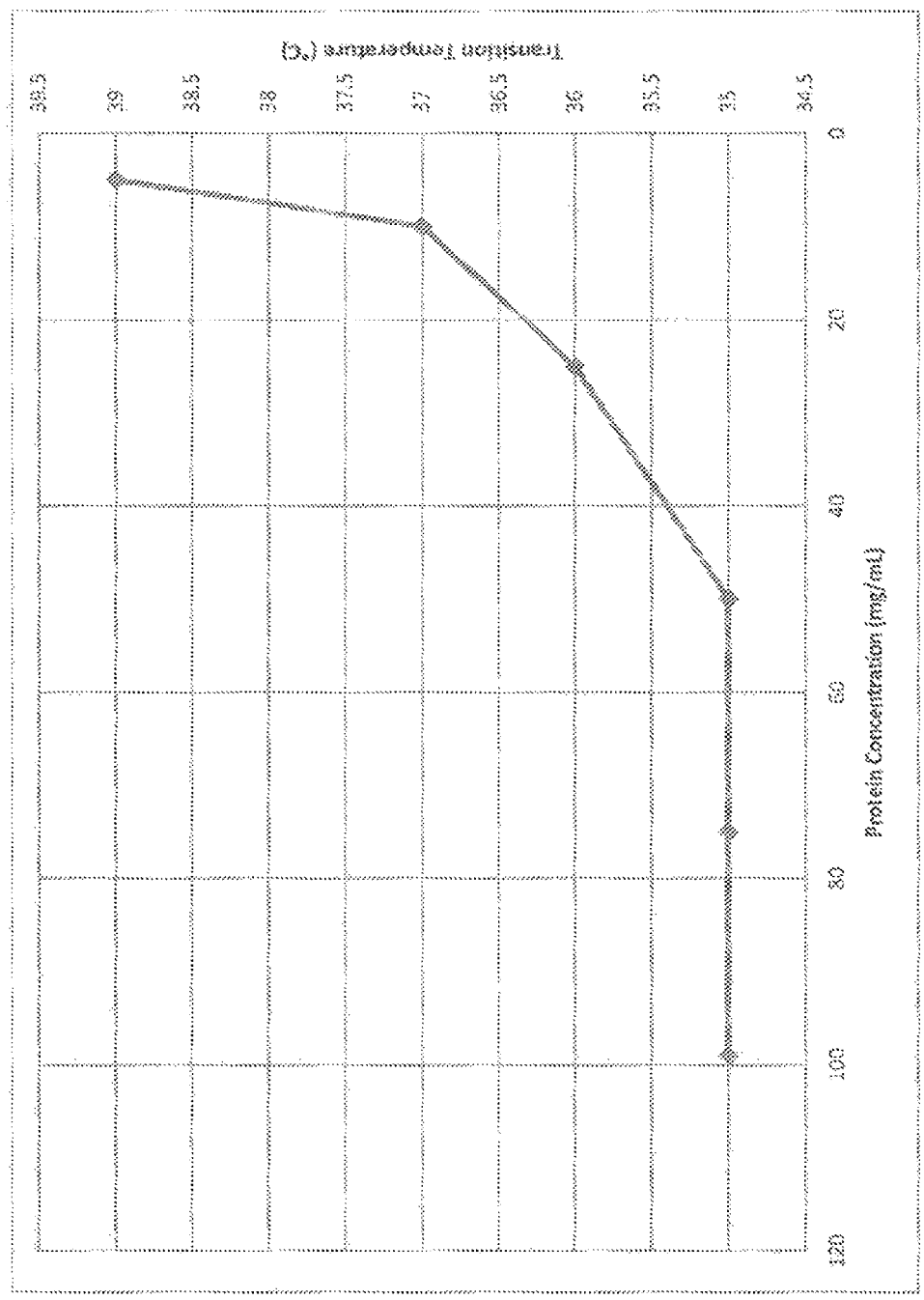
FIG. 5 shows that the ELP1 series transitions at just below 37° C. at relatively high protein concentration of about 10 mg/ml or more, allowing for sustained release formulations with relatively high amounts of active agents.

FIG. 4 shows that the ELP4 series (about 120 structural units) transitions at 37° C. at a protein concentration of less than about 0.01 mg/mL, allowing for sustained release formulations of low protein concentration. At higher concentrations the sustained release will be sufficiently slow to provide a depot like formulation. FIG. 5 shows that the ELP1 series transitions between 35 and 37° C. at relatively high protein concentration of about 10 mg/mL to about 100 mg/mL, or more, allowing for sustained release formulations with relatively high amounts of active agents.

Various formulations were prepared for PB1023 (GLP-1, A8G,7-37, ELP1-120) and PB1046 (M-VIP ELP1-120), at varying protein concentrations and ionic strength. Transition induced by 37° C. water bath was tested.

Table 1 shows determination of phase transition for formulations of PB1023 and PB1046, varied by protein concentration and ionic strength. As shown, formulations of at least 50 mg/mL PB1023 and with an ionic strength of at least that of 10 mM His and 55 mM NaCl, transitioned at 37° C. (with an approximate transition temperature of 35.5° C.). A formulation of 25 mg/mL of PB-1023 and an ionic strength of about normal saline also transitioned at 37° C. Formulations even as low as 1 mg/mL of PB1046 and having an ionic strength similar to normal saline transitioned at 37° C.

As shown in Table 2, Formulations of 25 mg/mL PB1023 in either: normal saline, DPBS, or 1× phosphate buffered saline, were sufficient to generate the desired transition property. Water alone did not support the desired transition property.

As shown in Table 3, a formulation of 25 mg/ml PB1023 transitions at 37° C. with an ionic strength equal to 50 mM NaCl.

Table 4, Table 5, and Table 6 show some buffer formulations in accordance with certain embodiments of the invention.

FIG. 6 shows a summary of pharmacokinetic parameters for GLP-1/ELP1-120 (also referred to herein as PB1023 or (Glymera) after SC administration of 0.3, 0.6, 0.9 and 1.35 mg/kg to adult subjects with type 2 diabetes mellitus.

Figure 7:
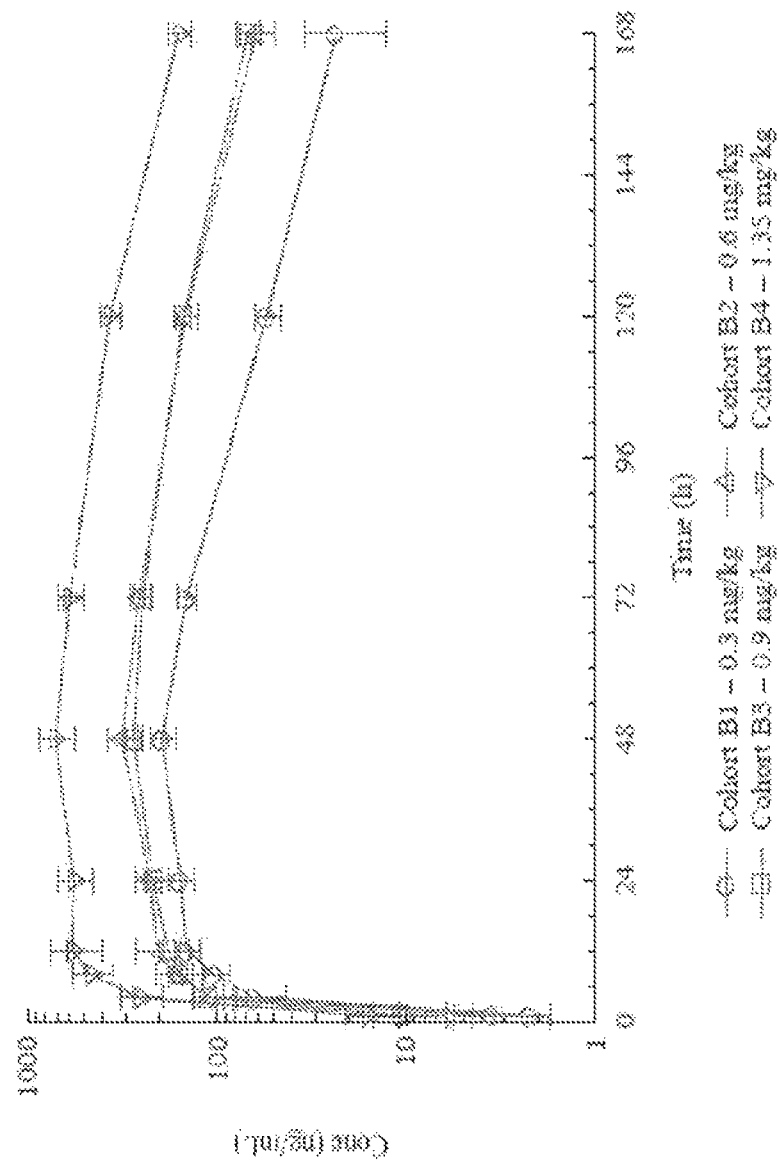
FIG. 7 shows the mean serum concentrations of Glp-1/ELP1-120 (also referred to herein as PB1023 or Glymera) after s.c. administration on day 0 of 0.3, 0.6, 0.9 and 1.35 mg/kg to adult subjects with type 2 diabetes mellitus (semi-logarithmic axes).

FIG. 7 shows the mean serum concentrations of GLP-1/ ELP1-120 (also referred to herein as PB1023 or Glymera) after s.c. administration on day 0 of 0.3, 0.6, 0.9 and 1.35 mg/kg to adult subjects with type 2 diabetes mellitus (semi-logarithmic axes).

Figure 8:
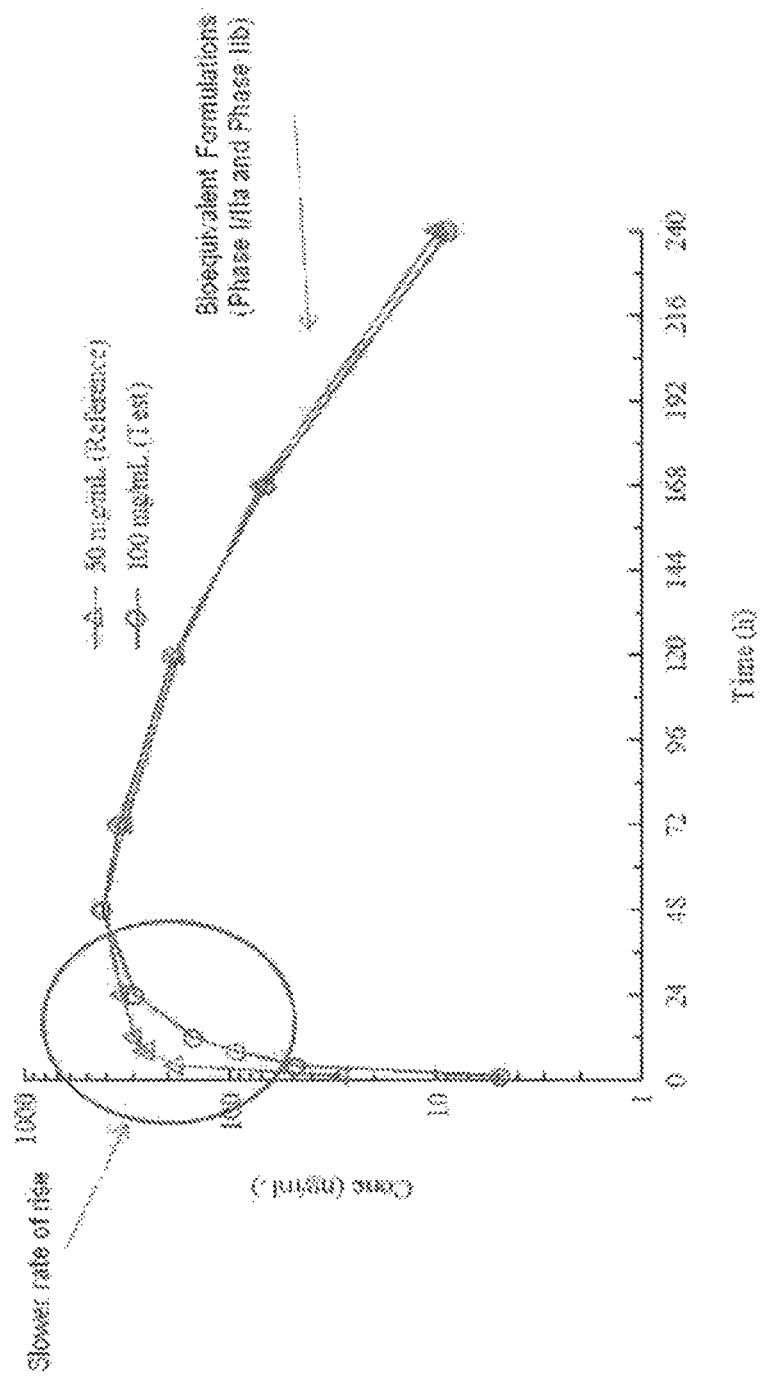
FIG. 8 shows the type 2 diabetes mellitus: Glymera program overview. pharmacokinetics crossover study. Mean serum concentrations of Glymera following s.c. administration of 90 mg as 50 mg/mL and 100 mg/mL formulations to adult subjects with type 2 diabetes mellitus are shown (semi-logarithmic axes).

FIG. 8 shows a type 2 diabetes mellitus: Glymera program overview pharmacokinetics crossover study. Mean serum concentrations of Glymera following s.c. administration of 90 mg as 50 mg/mL and 100 mg/mL formulations to adult subjects with type 2 diabetes mellitus are shown (semi-logarithmic axes). It is noted that the time courses for mean serum distribution for the 50 mg/mL and 100 mg/mL are nearly equivalent on the whole, except that the 100 mg/mL dose bursts into the blood stream slower than the 50 mg/mL dose (i.e. the 100 mg/mL data set has a slower rate of rise).

FIG. 9 shows a summary of pharmacokinetic parameters for ELP1-120 (also referred to herein as PB1023 or Glymera) after s.c. administration of 90 mg as 50 mg/mL, and 100 mg/mL formulations to adult subjects with type 2 diabetes mellitus.

Cold Administration

An open label, single dose, 2-period, 2-treatment, 2-sequence crossover design study to compare the pharmacokinetic profile of PB1023 after a single dose administered by subcutaneous (SC) injection of 50 mg/mL and 100 mg/mL formulations, the latter at room temperature and cold (2° to 8° C.) undertaken. Adult subjects with Type 2 Diabetes Mellitus (T2DM) were given a single 90 mg dose of each product at room temperature according to a randomized, 2-period, 2-sequence design. Subjects then returned for a $3^{rd}$ treatment, 100 mg/mL administered cold (2° to 8° C.). Ten (10) subjects were enrolled and all subjects completed the 2 randomized treatments. Eight (8) subjects returned for the $3^{rd}$ period. The analysis population was therefore comprised of 10 subjects for the comparison of 100 mg/mL and 50 mg/mL and 8 subjects for the comparison of 100 mg/mL at room temperature and as a cold formulation.

The pharmacokinetic parameters for PB1023 and the associated statistical analyses are summarized in the FIGS. 10 and 11.

The geometric mean ratios (GMR) for Cmax, AUC(0-t), and AUC(inf) for the comparison of the 100 mg/mL to 50 mg/mL formulations ranged from 94.79% to 99.97% and all associated 90% confidence intervals (CI) were contained within 80.00% and 125.00%, demonstrating bioequivalence between the 2 formulations.

When administered cold (2° to 8° C.), there was a decrease in Cmax, AUC(0-t), and AUC(inf) with GNIRs of 68.66%, 79.90%, and 73.30%, respectively, and the lower limits of all 3 CIs were substantially below 80.00%. This demonstrates a significant decrease in absorption when PB1023 was administered cold.

The 100 mg/mL formulation of PB1023 was bioequivalent to the 50 mg/mL formulation after administration to adult subjects with T2DM. Administration of PB1023 as a cold formulation (2° to 8° C.) resulted in a significant decrease in absorption.

A hypotonic formulation (containing 20 mM histidine only) of PB1023 Injection at a concentration of 50 mg/mL (formulated in 20 mM histidine) was diluted to 25 mL with 0.9% sodium chloride to render the final formulation nearly isotonic prior to administration. To eliminate the need for tonicity adjustment by study personnel, an isotonic formulation (containing 20 mM histidine and 110 mM NaCl for tonicity) at a concentration of 100 mg/mL was manufactured for use in future clinical trials.

This study evaluated the impact on the rate of absorption when the 100 mg/mL formulation is injected cold (2° to 8° C.). A purpose of this study was to compare the pharmacokinetic profile of PB1023 Injection after administration of the two formulations and the effect of cold administration on absorption.

This was an open label, single dose, 3-period, 3-treatment, 2-sequence crossover/sequential design study of the pharmacokinetics of PB1023 after a single dose administered by subcutaneous (SC) injection of 50 mg/mL and 100 mg/mL formulations at room temperature and 100 mg/mL as a cold formulation. Adult subjects with T2DM received, according to a randomization schedule, a dose of one of the PB1023 formulations at each visit.

Blood samples were collected before and 1, 4, 8, 12, 24, 48, 72, 120, 168, and 240 hours after dosing. Blood samples were centrifuged and the resultant serum was transferred to two (2) clearly labeled polypropylene tubes and stored frozen until assay.

All pharmacokinetic parameters were calculated using non-compartmental analysis. Only those serum concentrations equal to or greater than the LOQ (9.76 mg/mL) were used in the analysis. Actual sampling times were used in all pharmacokinetic analyses. Per protocol times were used to calculate mean serum concentrations for graphical displays.

The maximum serum concentration (Cmax) and time to Cmax (Tmax) were taken directly from the data. The elimination rate constant, λz, was calculated as the negative of the slope of the terminal log-linear segment of the serum concentration-time curve. The range of data used for each subject and treatment was determined by visual inspection of a semi-logarithmic plot of concentration vs. time. Elimination half-life (t½) was calculated according to the following equation.

$$t\frac{1}{2} = \frac{0.693}{\lambda z}$$

Area under the curve from zero to the final sample with a concentration≥LOQ [AUC(0-t)] was calculated using the linear trapezoidal method and extrapolated to infinity [AUC (inf)] using $$AUC(inf) = AUC(0-t) + \frac{C_{tf}}{\lambda z}$$

where $C_{tf}$ is the final concentration LOQ.
Clearance (CL/F) and volume of distribution (Vz/F), uncorrected for bioavailability (F) were calculated according to $$CL/F = \frac{Dose}{AUC(inf)} \text{ and } Vz/F = \frac{Dose}{AUC(inf) \times \lambda z},$$

respectively.

All pharmacokinetic calculations were done and individual subject plasma concentration-time graphs were prepared using SAS® for Windows® Version 9.3. Graphs of mean plasma concentration vs. time were prepared using SigmaPlot for Windows Version 12.2.

Comparison of the kinetic parameters Cmax, AUC(04), and AUC(inf) for PB1023 between the test (100 mg/mL) and reference (50 mg/mL) formulations was done using an analysis of variance statistical model (ANOVA) with sequence, subject within sequence, treatment, and period as the classification variables, using the natural logarithms of the data. Comparison of Cmax, AUC(0-t), and AUC(inf) after administration of PB1023 as a cold formulation and at room temperature was done using an ANOVA with subject and treatment as the classification variables, using the natural logarithms of the data.

For both analyses, confidence intervals (CI) (90%) were constructed for the geometric mean ratio (GMR), test-to-reference, of the three parameters using the log-transformed data and the two one-sided t-tests procedure. The GMRs and CI limits were exponentiated back to the original scale.

The within-subject coefficient of variation (WSCV) of each natural log-transformed parameter was calculated according to $$WSCV = 100\% \times \sqrt{e^{MSE} - 1}$$

where MSE is the mean squared error from the analysis of variance.

All statistical analyses were done using SAS® for Windows® Version 9.3.

Ten (10) subjects were enrolled and all subjects completed the 2 randomized treatments. Eight (8) subjects returned for the 3rd period. The analysis population was therefore comprised of 10 subjects for the comparison of 100 mg/mL, and 50 mg/mL and 8 subjects for the comparison of 100 mg/mL, as room temperature formulation and as a cold formulation.

Pharmacokinetics

Comparison of 100 mg/mL and 50 mg/mL Formulations

Figure 12:
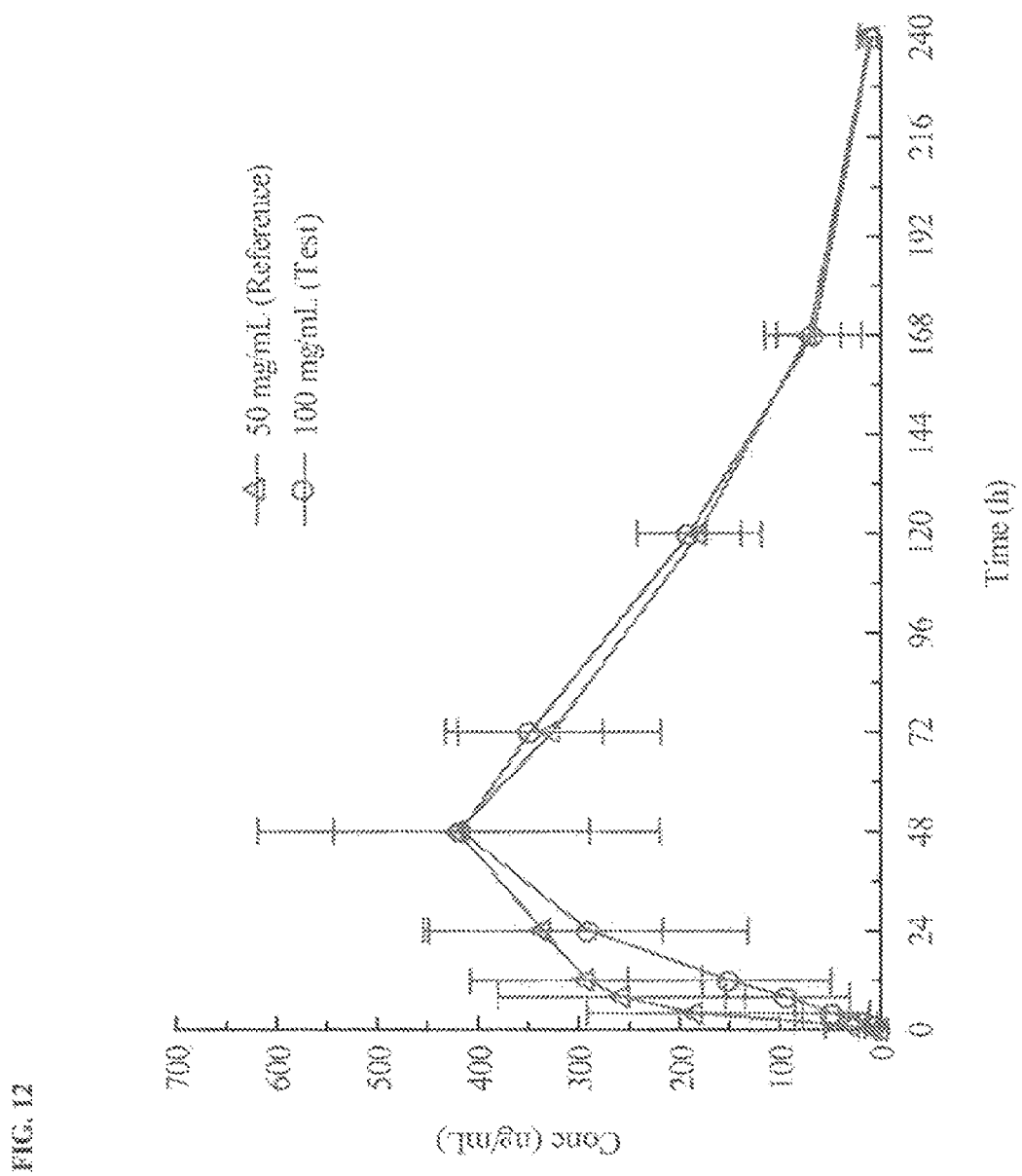
FIG. 12 shows the mean±standard deviation serum concentrations of PB1023 after SC administration of 90 mg as 50 mg/mL and 100 mg/mL formulations to adult subjects with T2DM—linear axes.
Figure 13:
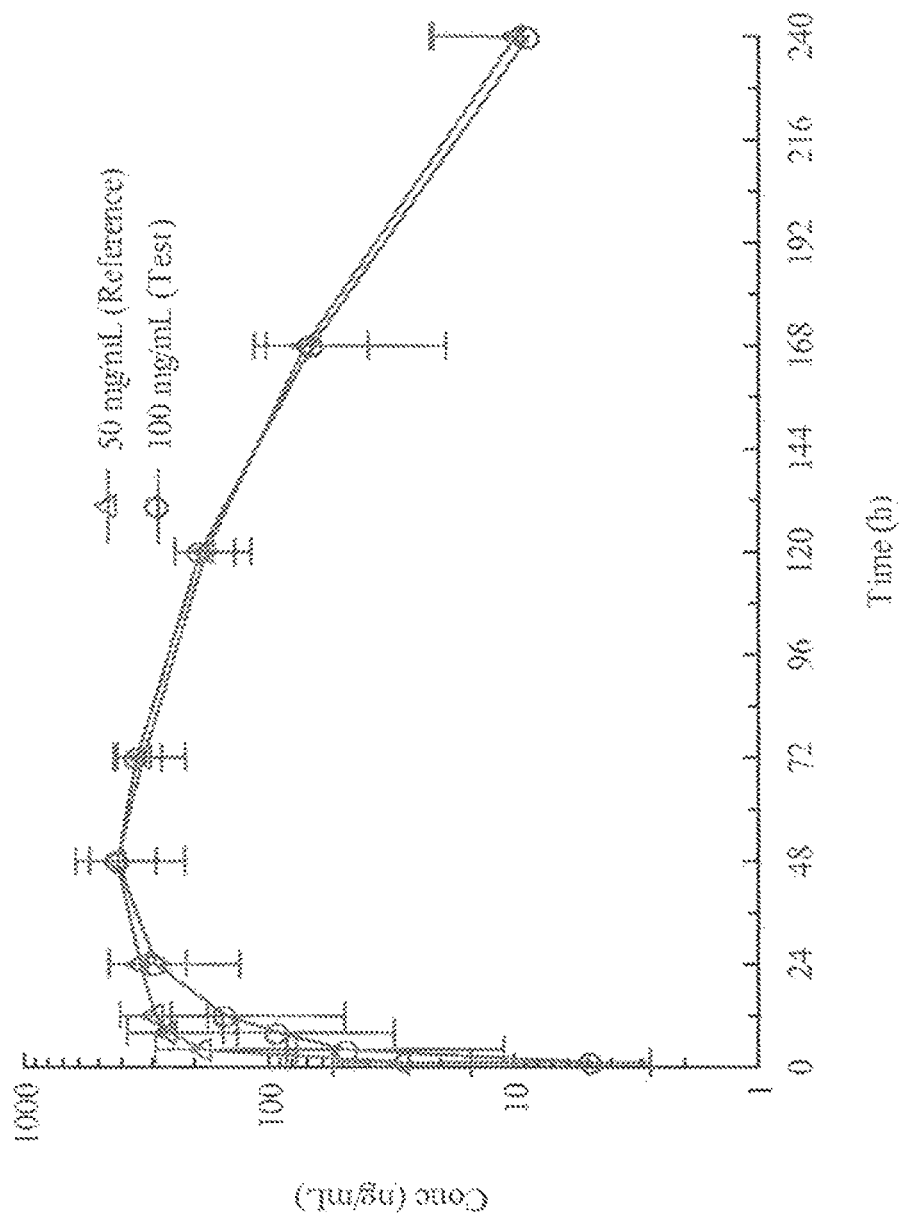
FIG. 13 shows the mean±standard deviation serum concentrations of PB1023 after SC administration of 90 mg as 50 mg/mL, and 100 mg/mL formulations to adult subjects with T2DM—semi-logarithmic axes.

As shown in FIG. 12 (linear axes) and FIG. 13 (semi-logarithmic axes), the mean serum PB1023 concentrations increased at a faster rate after administration of the 50 mg/mL formulation compared to the 100 mg/mL formulation; this was also observed for the majority of the individual subjects. However, mean concentrations from 48 hours onward were essentially the same for both formulations (FIG. 12). The mean values for Cmax, AUC(0-t), and AUC(inf) were comparable for both formulations (FIG. 14) with GMRs ranging from 94.79% to 99.97% and all associated 90% CI were with 80.00% to 125.00% (FIG. 1), demonstrating bioequivalence between the 2 formulations.

The median Tmax was similar for the 50 mg/mL and 100 mg/mL formulations (49.4 h and 48.4 h, respectively) as were the mean values for t½ and CL/F (FIG. 14)

Figure 16:
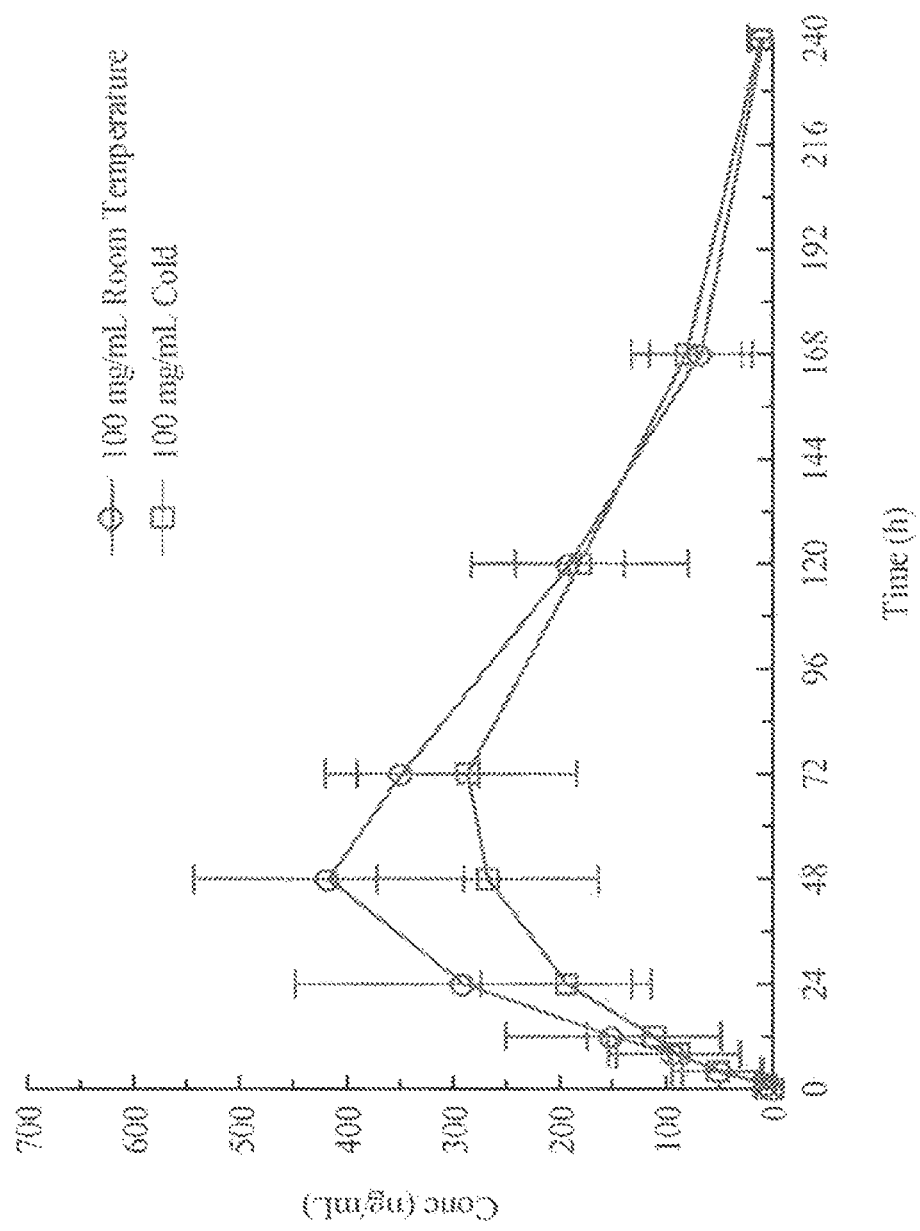
FIG. 16 shows the mean±standard deviation serum concentrations of PB1023 after SC administration of 90 mg as the 100 mg/mL formulation at room temperature and 100 mg/mL cold (2° to 8° C.) to adult subjects with T2DM linear axes.
Figure 17:
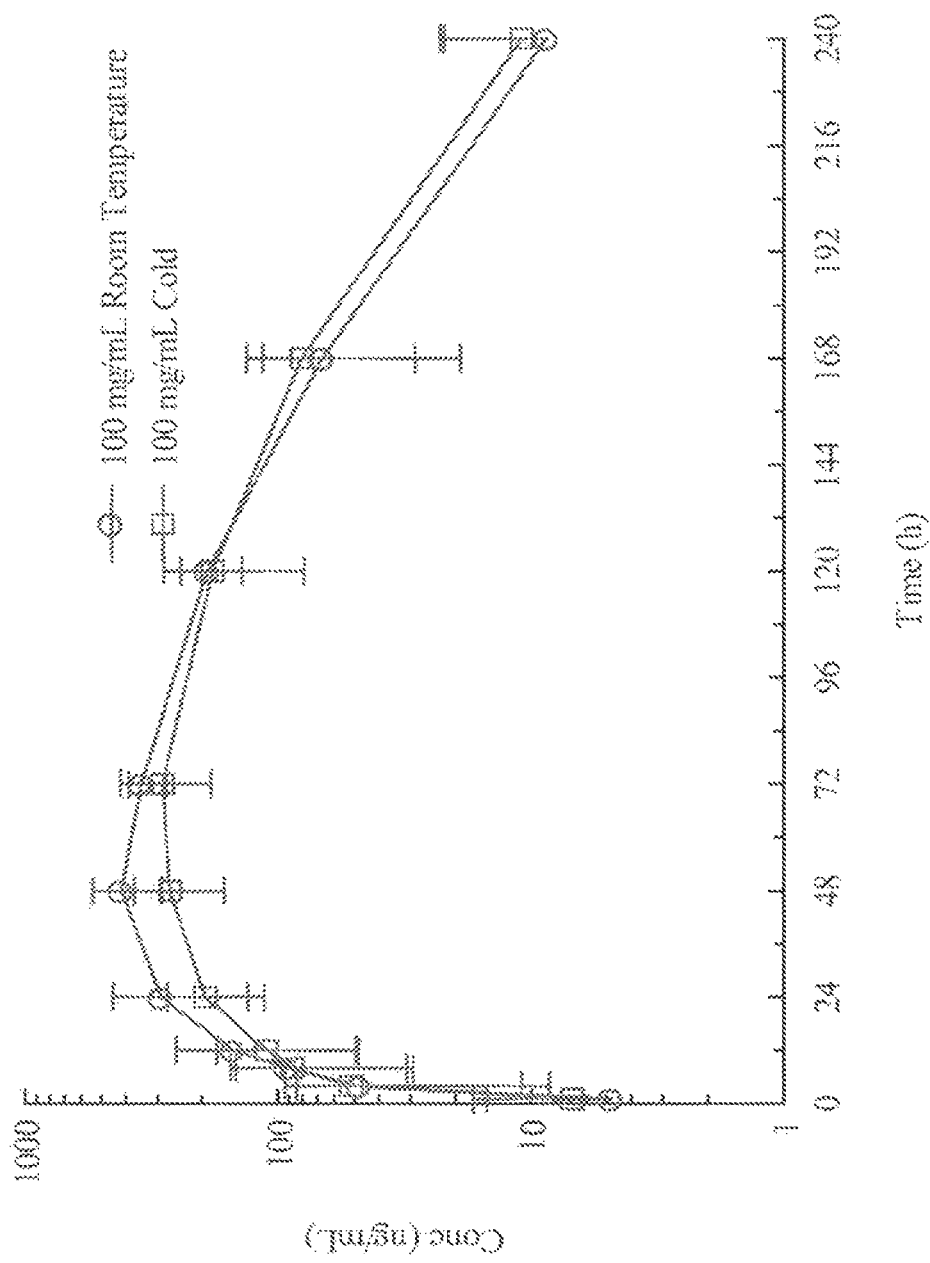
FIG. 17 shows the mean±standard deviation serum concentrations of PB1023 after SC administration of 90 mg as the 100 mg/mL, formulation at room temperature and 100 mg/mL cold (2° to 8° C.) to adult subjects with T2DM semi-logarithmic axes.

Comparison of the 100 mg/mL Formulation Administered Cold (2° to 8° and at Room Temperature As shown FIG. 16 (linear axes) and FIG. 17 (semi-logarithmic axes), the mean serum PB1023 concentrations were lower when the 100 mg/mL formulation was administered under cold (2° to 8° C.) compared to room temperature conditions; this was also observed for the majority but not all of the individual subjects. The mean values for Cmax, AUC(0-t), and AUC(inf) were lower when PB1023 was administered cold for both formulations (FIG. 18) with GMRs of 68.66%, 79.90%, and 73.30%, respectively, and the lower limits of all 3 CIs were substantially below 80.00% (FIG. 19). This demonstrates a significant decrease in absorption when PB1023 was administered cold.

The median Tmax was about 50% longer when PB1023 was injected as a cold formulation (FIG. 18), suggesting, but not wishing to be bound by theory, a slower rate of absorption in addition to the lower bioavailability. The mean t½ increased from 30.8±4.95 h to 40.2±20.1 h (FIG. 18), most likely a consequence of the slower absorption and "flip-flop" kinetics.

The 100 mg/mL, formulation of PB1023 was bioequivalent to the 50 mg/ml, formulation after administration to adult subjects with T2DM. Administration of PB1023 as a cold formulation (2° to 8° C.) resulted in a significant decrease in absorption.

TABLE 1

Initial Transition Experiments Using a 37° C. Waterbath and Visual Interpretation of Results

| Drug/Formulation | Dilution Buffer | Final Concentration/ Formulation | Transition in 37° C. waterbath | Cary Transition Temperature |
|---|---|---|---|---|
| 100 mg/mL PB1023 20 mM His, 110 mM NaCl | NA | 100 mg/mL PB1023 20 mM His, 100 mM NaCl | Yes | ~34.9° C. |
| 100 mg/mL PB1023 20 mM His, 110 mM NaCl | Water | 90 mg/mL 18 mM His, 99 mM NaCl | Yes | |
| 100 mg/mL PB1023 20 mM His, 100 mM NaCl | Water | 80 mg/mL 16 mM His, 88 mM NaCl | Yes | |
| 100 mg/mL PB1023 20 mM His, 100 mM NaCl | Water | 50 mg/mL 10 mM His, 55 mM NaCl | Yes | |
| 50 mg/mL PB1023 20 mM His, 100 mM NaCl | NA | 50 mg/mL PB1023 20 mM Histidine | No | ~49° C. |
| 50 mg/mL PB1023 20 mM Histidine | Normal Saline (0.9% NaCl) | 25 mg/mL 10 mM Histidine, 75 mM NaCl | Yes | |
| 40 mg/mL PB1046 20 mM His, 75 mM NaCl | NA | 40 mg/mL PB1046 20 mM His, 75 mM NaCl | Yes | |
| 40 mg/mL PB1046 20 mM His, 75 mM NaCl | Normal Saline (0.9% NaCl) | 12 mg/mL PB1046 | Yes | |
| 40 mg/mL PB1046 20 mM His, 75 mM NaCl | Normal Saline (0.9% NaCl) | 1 mg/mL PB1046 | Yes | |

TABLE 2

Transition Temperature Experiments Using Various Dilution Buffers

| Drug/Formulation | Dilution Buffer | Final Concentration | Transition in 37° C. waterbath | Cary Transition Temperature |
|---|---|---|---|---|
| 50 mg/mL PB1023 20 mM Histidine | Water | 25 mg/mL PB1023 | No | ~51.1 |
| 50 mg/mL PB1023 20 mM Histidine | Normal Saline (0.9% NaCl) | 25 mg/mL PB1023 | Yes | ~36.5 |
| 50 mg/mL PB1023 20 mM Histidine | DPBS w/MG and Ca | 25 mg/mL PB1023 | Yes | |
| 50 mg/mL PB1023 20 mM Histidine | DPBS w/out MG and Ca | 25 mg/mL PB1023 | Yes | |
| 50 mg/mL PB1023 20 mM Histidine | IX PBS | 25 mg/mL PB1023 | Yes | |

TABLE 3

Transition Experiments Varying Salt Concentration

| Drug/Formulation | Dilution Buffer | Final Concentration/ Formulation | Transition in 37° C. waterbath | Cary Transition Temperature |
|---|---|---|---|---|
| 50 mg/mL PB1023 20 mM Histidine | NaCl and Water | 25 mg/mL PB1023 50 mM NaCl | Yes | ~37° C. |
| 50 mg/mL PB1023 20 mM Histidine | NaCl and Water | 25 mg/mL PB1023 40 mM NaCl | | ~37° C. |
| 50 mg/mL PB1023 20 mM Histidine | NaCl and Water | 25 mg/mL PB1023 30 mM NaCl | | ~37° C. |
| 50 mg/mL PB1023 20 mM Histidine | NaCl and Water | 25 mg/mL PB1023 25 mM NaCl | Not Visible | ~37° C. |
| 50 mg/mL PB1023 20 mM Histidine | NaCl and Water | 25 mg/mL PB1023 12.5 mM NaCl | Not Visible | |
| 50 mg/mL PB1023 20 mM Histidine | NaCl and Water | 25 mg/mL PB1023 10 mM NaCl | | ~37° C. |
| 50 mg/mL PB1023 20 mM Histidine | NaCl and Water | 25 mg/mL PB1023 6.25 mM NaCl | Not Visible | |
| 50 mg/mL PB1023 20 mM Histidine | NaCl and Water | 25 mg/mL PB1023 3.125 mM NaCl | Not Visible | |

TABLE 3-continued

Transition Experiments Varying Salt Concentration

| Drug/Formulation | Dilution Buffer | Final Concentration/ Formulation | Transition in 37° C. waterbath | Cary Transition Temperature |
|---|---|---|---|---|
| 50 mg/mL PB1023 20 mM Histidine | NaCl and Water | 25 mg/mL PB1023 1.56 mM NaCl | Not Visible | |
| 50 mg/mL PB1023 20 mM Histidine | NaCl and Water | 25 mg/mL PB1023 1 mM NaCl | | ~40.3° C. |
| 50 mg/mL PB1023 20 mM Histidine | NaCl and Water | 25 mg/mL PB1023 0.78 mM NaCl | Not Visible | |

TABLE 4

Buffer Formulation-DPBS with Mg and Ca

| COMPONENTS | Molecular Weight | Concentration (mg/L) | mM |
|---|---|---|---|
| Inorganic Salts | | | |
| Calcium Chloride ($CaCl_2$) (anhyd.) | 111 | 100 | 0.901 |
| Magnesium Chloride ($MgCl_2$—6H20) | 203 | 100 | 0.493 |
| Potassium Chloride (KCl) | 75 | 200 | 2.67 |
| Potassium Phosphate monobasic ($KH_2PO_4$) | 136 | 200 | 1.47 |
| Sodium Chloride (NaCl) | 58 | 8000 | 137.93 |
| Sodium Phosphate dibasic ($Na_2HPO_4$—$7H_2O$) | 268 | 2160 | 8.06 |

TABLE 5

Buffer Formulation-DPBS without Mg and Ca

| COMPONENTS | Molecular Weight | Concentration (mg/L) | mM |
|---|---|---|---|
| Inorganic Salts | | | |
| Potassium Chloride (KCl) | 75 | 200 | 2.67 |
| Potassium Phosphate monobasic ($KH_2PO_4$) | 136 | 200 | 1.47 |
| Sodium Chloride (NaCl) | 58 | 8000 | 137.93 |
| Sodium Phosphate dibasic ($Na_2HPO_4$—$7H_2O$) | 268 | 2160 | 8.06 |

TABLE 6

Buffer Formulation-1x PBS pH 7.4

| COMPONENTS | Molecular Weight | Concentration (mg/L) | mM |
|---|---|---|---|
| Inorganic Salts | | | |
| Potassium Phosphate monobasic ($Kh_2PO_4$) | 136 | 144 | 1.06 |
| Sodium Chloride (NaCl) | 58 | 9000 | 155.17 |
| Sodium Phosphate dibasic ($Na_2HPO_4$—$7H_2O$) | 268 | 795 | 2.97 |

---

What is claimed is:

1. A method for administering to a subject in need thereof a sustained release formulation for systemic delivery comprising a therapeutic agent and one or more pharmaceutically acceptable excipients and/or diluents, wherein the therapeutic agent comprises a Vasoactive Intestinal Peptide (VIP) and an elastin-like peptide, wherein the elastin-like peptide comprises at least 90 repeating units of VPGXG (SEQ ID NO: 3), and wherein the formulation is administered at a temperature from about 2 to about 8° C., wherein administration of the formulation at a temperature from about 2 to about 8° C. slows absorption of the therapeutic agent compared to absorption of the same therapeutic agent administered at room temperature.

2. The method of claim 1, wherein the formulation provides a flat PK profile upon administration, as compared to the PK profile for the Vasoactive Intestinal Peptide (VIP) in the absence of the ELP.

3. The method of claim 2, wherein the PK profile has a shallow Cmax and/or low ratio of peak to trough and/or long Tmax.

4. The method of claim 1, wherein the ELP comprises 120 repeating units of SEQ ID NO: 3, where each X is selected from V, G, and A, and wherein the ratio of V:G:A is about 5:3:2.

5. The method of claim 4, wherein the ELP comprises SEQ ID NO: 14.

6. The method of claim 1, wherein the subject is human.

7. The method of claim 1, wherein therapeutic agent is a recombinant fusion protein of the Vasoactive Intestinal Peptide (VIP) and the ELP.

8. The method of claim 7, wherein the Vasoactive Intestinal Peptide (VIP) has a circulatory half-life in the range of from about 30 seconds to about 10 hours.

9. The method of claim 1, wherein the Vasoactive Intestinal Peptide (VIP) is a VPAC-2 selective peptide.

10. The method of claim 1, wherein the Vasoactive Intestinal Peptide (VIP) has an additional Methionine at the N-terminus.

11. The method of claim 1, wherein the therapeutic agent is present in the range of about 0.5 mg/mL to about 200 mg/mL.

12. The method of claim 1, wherein the therapeutic agent does not form a phase-transitioned matrix at storage conditions.

13. The method of claim 12, wherein the storage conditions are less than about 40° C.

14. The method of claim 1, wherein the formulation comprises histidine and sodium chloride.

15. The method of claim 14, wherein the formulation comprises 20 mM histidine and 75 mM sodium chloride.

16. The method of claim 1, wherein the formulation is packaged in the form of pre-dosed pens or syringes for administration from about one to about five times per month.

17. The method of claim 1, wherein the formulation is administered from about 1 to about 8 times per month.

18. The method of claim 17, wherein the formulation is administered about weekly.

19. The method of claim 17, wherein the formulation is administered subcutaneously or intramuscularly.

20. A method for administering to a subject in need thereof a sustained release formulation for systemic delivery comprising a therapeutic agent and one or more pharmaceutically acceptable excipients and/or diluents, wherein the therapeutic agent comprises a VPAC-2 selective Vasoactive Intestinal Peptide (VIP) comprising an additional Methionine at the N-terminus and an elastin-like peptide, wherein the elastin-like peptide comprises 120 repeating units of SEQ ID NO: 3, where each X is selected from V, G, and A, and wherein the ratio of V:G:A is about 5:3:2, and wherein the formulation is administered at a temperature from about 2 to about 8° C., wherein administration of the formulation at a temperature from about 2 to about 8° C. slows absorption of the therapeutic agent compared to absorption of the same therapeutic agent administered at room temperature.

* * * * *